(12) United States Patent
Peumans et al.

(10) Patent No.: US 11,684,915 B2
(45) Date of Patent: Jun. 27, 2023

(54) COMPACT FLUID ANALYSIS DEVICE AND METHOD TO FABRICATE

(71) Applicant: IMEC VZW, Leuven (BE)

(72) Inventors: Peter Peumans, Herfelingen (BE); Liesbet Lagae, Leuven (BE); Paolo Fiorini, Brussels (BE)

(73) Assignee: IMEC VZW, Leuven (BE)

( * ) Notice: Subject to any disclaimer, the term of this patent is extended or adjusted under 35 U.S.C. 154(b) by 0 days.

(21) Appl. No.: 16/058,828

(22) Filed: Aug. 8, 2018

(65) Prior Publication Data

US 2018/0361381 A1 Dec. 20, 2018

Related U.S. Application Data

(62) Division of application No. 15/529,441, filed as application No. PCT/EP2015/077412 on Nov. 24, 2015, now abandoned.

(30) Foreign Application Priority Data

Nov. 26, 2014 (EP) .................................... 14194854

(51) Int. Cl.
   *B01L 3/00* (2006.01)
   *A61B 5/151* (2006.01)
   (Continued)

(52) U.S. Cl.
   CPC ........ *B01L 3/502715* (2013.01); *A61B 5/151* (2013.01); *A61B 5/157* (2013.01);
   (Continued)

(58) Field of Classification Search
   CPC ............ H01L 51/4246; B01L 3/50273; B01L 2400/0406; B01L 2400/086;
   (Continued)

(56) References Cited

U.S. PATENT DOCUMENTS 5,006,202 A 4/1991 Hawkins et al.
5,055,203 A * 10/1991 Columbus ............. B01L 3/5021
                                                210/741
(Continued)

FOREIGN PATENT DOCUMENTS

EP   2011574 A1   1/2009
WO   98/50154     11/1998
(Continued)

OTHER PUBLICATIONS

Tanaka, Hiroyuki et al., "Electrochemical Sensor with Dry Reagents Implemented in Lab-on-Chip for Single Nucleotide Polymorphism Detection," Japanese Journal of Applied Physics, vol. 53, Apr. 17, 2014, pp. 1-5.
(Continued)

*Primary Examiner* — Dean Kwak
(74) *Attorney, Agent, or Firm* — McDonnell Boehnen Hulbert & Berghoff LLP

(57) ABSTRACT

The present disclosure relates to a fluid analyzing device that includes a sensing device for analyzing a fluid sample. The sensing device includes a microchip configured for sensing the fluid sample, and a closed micro-fluidic component for propagating the fluid sample to the microchip. The fluid sample can be provided to the micro-fluidic component via an inlet of the fluid analyzing device. And a vacuum compartment, which is air-tight connected to the sensing device, can create in the micro-fluidic component a suction force suitable for propagating the fluid sample through the micro-fluidic component.

12 Claims, 17 Drawing Sheets

(51) Int. Cl.
*A61B 5/157* (2006.01)
*A61B 5/15* (2006.01)

(52) U.S. Cl.
CPC .. *A61B 5/150022* (2013.01); *A61B 5/150061* (2013.01); *A61B 5/150389* (2013.01); *B01L 3/5027* (2013.01); *B01L 3/50273* (2013.01); *A61B 2562/028* (2013.01); *B01L 2200/10* (2013.01); *B01L 2300/041* (2013.01); *B01L 2300/046* (2013.01); *B01L 2300/0654* (2013.01); *B01L 2300/0672* (2013.01); *B01L 2300/0816* (2013.01); *B01L 2300/18* (2013.01); *B01L 2400/0406* (2013.01); *B01L 2400/049* (2013.01)

(58) Field of Classification Search
CPC ....... B01L 2400/0688; B01L 3/502707; B01L 3/502715; B01L 2300/046; B01L 2300/0636; B01L 2300/0645; B01L 2300/0816; B01L 7/52; B01L 2300/0663; B01L 2300/0681; B01L 2300/0819; B01L 2300/0887; B01L 2300/123; B01L 2300/1833; B01L 2400/0415; B01L 2300/0864; B01L 2400/0427; B01L 3/502738; B01L 3/502746; B01L 2200/10; B01L 2200/147; B01L 2300/041; B01L 2300/0672; B01L 2300/18; B01L 2300/1805; B01L 2300/1883; B01L 2400/049; B01L 3/50857; B01L 3/565; B01L 9/527
USPC .................... 422/501–505, 508, 410, 546
See application file for complete search history.

(56) References Cited

U.S. PATENT DOCUMENTS

| | | |
|---|---|---|
| 5,385,635 A | 1/1995 | O'Neill |
| 5,919,712 A | 7/1999 | Herron et al. |
| 6,123,820 A | 9/2000 | Bergkuist |
| 2002/0022261 A1 | 2/2002 | Anderson et al. |
| 2002/0142471 A1* | 10/2002 | Handique ......... B01L 3/502738 |
| | | 436/53 |
| 2003/0019522 A1* | 1/2003 | Parunak .................. F15C 3/002 |
| | | 137/251.1 |
| 2006/0078475 A1 | 4/2006 | Tai et al. |
| 2006/0153736 A1* | 7/2006 | Kalra ..................... B01L 3/508 |
| | | 422/400 |
| 2007/0172388 A1 | 7/2007 | Padmanabhan et al. |
| 2007/0281288 A1* | 12/2007 | Belkin ............. B01L 3/502715 |
| | | 435/4 |
| 2009/0169427 A1 | 7/2009 | Supriya et al. |
| 2009/0317302 A1 | 12/2009 | McAvoy et al. |
| 2011/0201099 A1 | 8/2011 | Anderson et al. |
| 2013/0189796 A1 | 7/2013 | Kanaley et al. |
| 2014/0322706 A1* | 10/2014 | Kayyem .......... G01N 35/00732 |
| | | 435/6.11 |
| 2015/0093816 A1 | 4/2015 | Lagae et al. |
| 2015/0320349 A1* | 11/2015 | Haghgooie .......... A61B 5/1438 |
| | | 210/294 |
| 2016/0199834 A1* | 7/2016 | Bransky ............ B01L 3/502715 |
| | | 435/309.1 |

FOREIGN PATENT DOCUMENTS

WO 2012/054904 A2 4/2012
WO WO 2014/187926 11/2014

OTHER PUBLICATIONS

PCT International Search Report and Written Opinion, PCT International Application No. PCT/EP2015/077412, dated Mar. 1, 2016, 8 pages.
PCT International Search Report and Written Opinion, PCT International Application No. PCT/EP2015/077439, dated Feb. 15, 2016, 8 pages.
Lee, Hakho et al., "IC/Microfuidic Hybrid System for Magnetic Manipulation of Biological Cells", IEEE Journal of Solid-State Circuits, vol. 41, No. 6, Jun. 6, 2006, pp. 1471-1480.

* cited by examiner

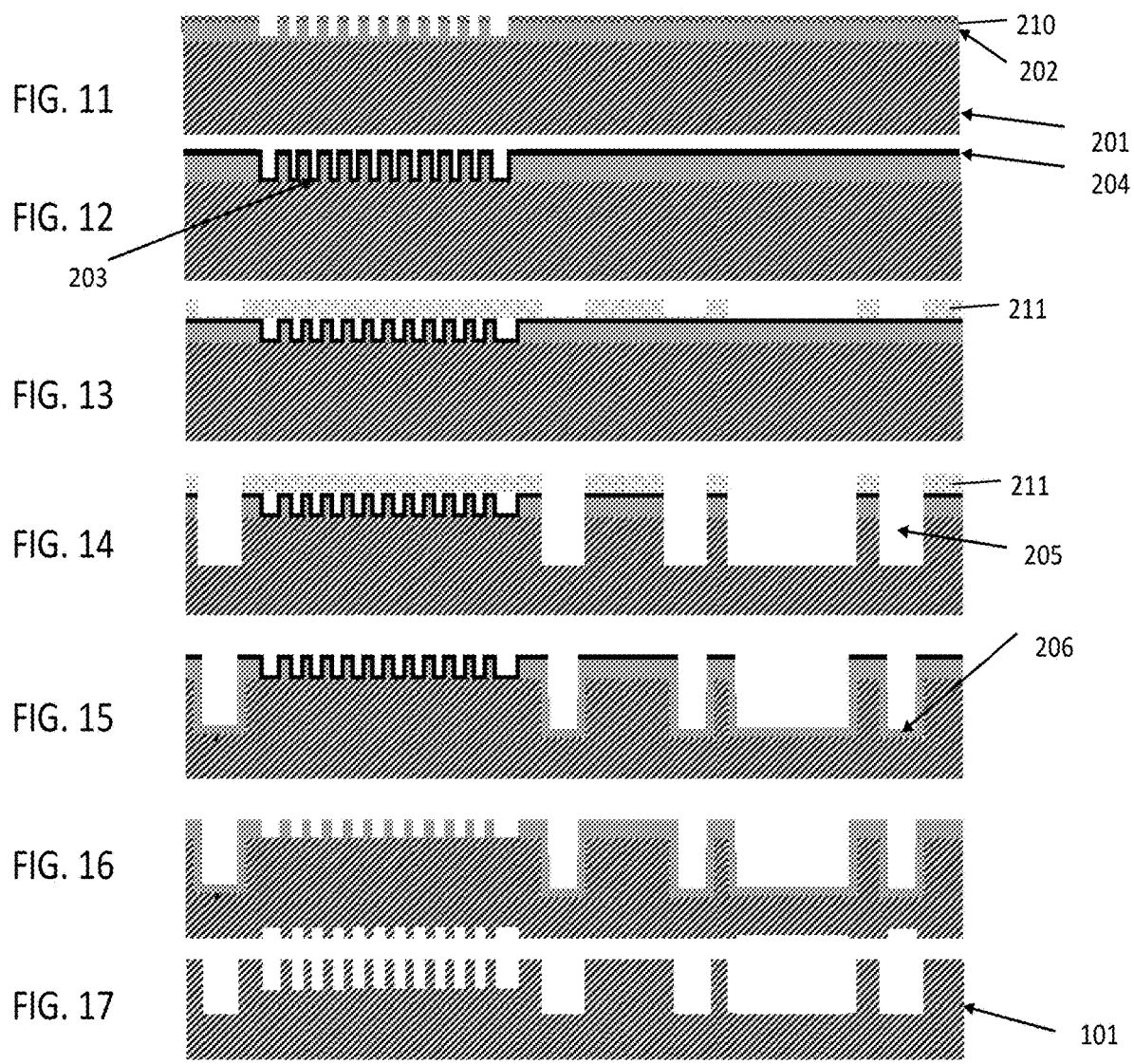

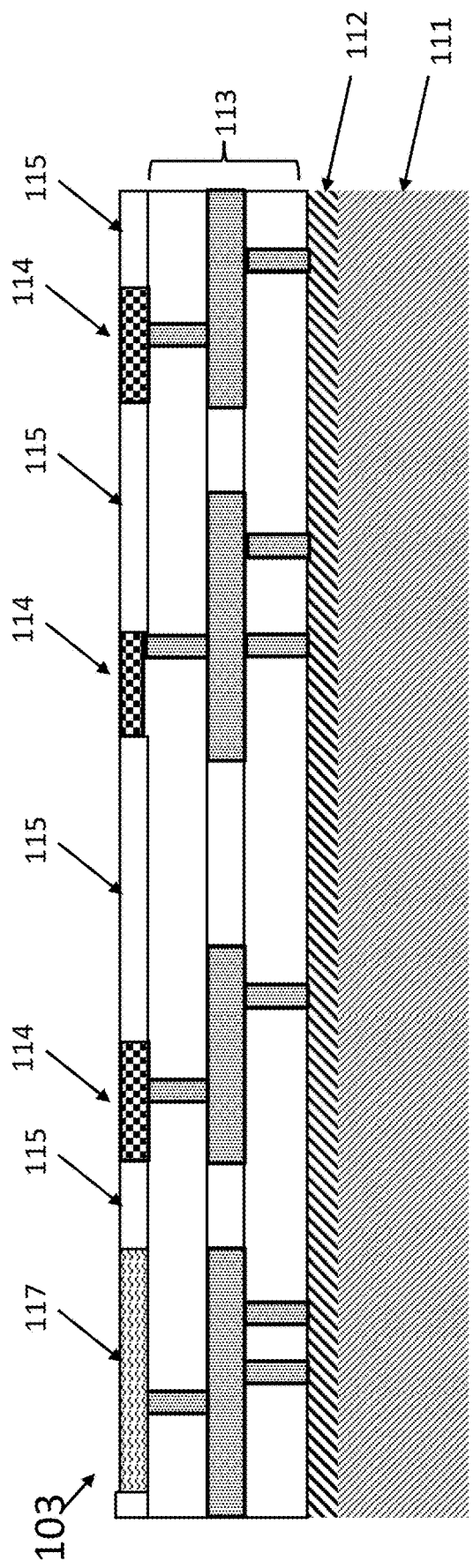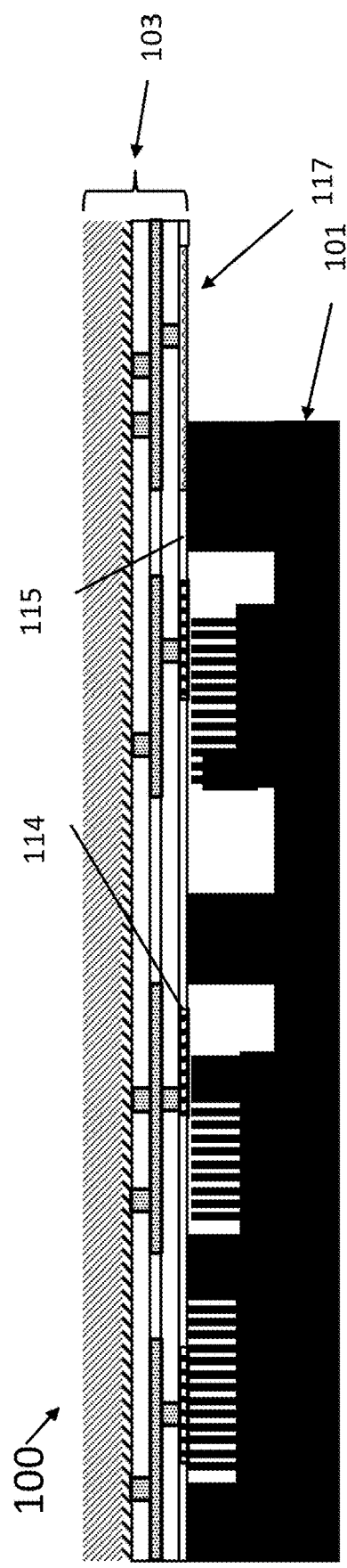
FIG. 21
FIG. 22

COMPACT FLUID ANALYSIS DEVICE AND METHOD TO FABRICATE

CROSS-REFERENCE TO RELATED APPLICATIONS

The present application is a divisional of U.S. application Ser. No. 15/529,441, filed on May 24, 2017, which is a 35 U.S.C. 371 National Application of PCT/EP2015/077412 filed Nov. 24, 2015, which claims priority to European Patent Application No. 14194854.7 filed on Nov. 26, 2014, the contents of each of which are hereby incorporated by reference.

TECHNICAL FIELD

The present disclosure relates to medical devices for fluid analysis. In particular, the present disclosure is related to compact devices, e.g., medical devices, for the analysis of a fluid sample. In particular, the present disclosure is related to fully integrated devices, such as lab-on-a-chip devices, for the analysis of bodily fluid samples.

BACKGROUND

A disadvantage of conventional point-of-care devices for the analysis of blood is their size which depends on the different components needed to perform analysis of blood. In these devices, external pumps are part of the point of care instrument. In some devices, miniature scale pumps are used to propagate a sample through the fluidic channels of the device. The use of pumps increases the size and cost of the device which makes them less suitable for usage as a disposable device. Current disposable devices are typically inserted in expensive read-out instruments, with many non-disposable electronic or optical components to detect the biochemical reactions taking place in the disposable device. Another disadvantage of state of the art point of care devices is their fabrication cost.

Other state of the art devices are lateral flow test strips. These test strips are usually fabricated from cellulose which does not allow precise control of the flow of a fluid sample propagating through the test strips, which can limit the applicability of these devices.

There is a need for a low-cost, easy to use, disposable, compact device for the fully integrated analysis of a fluid sample.

SUMMARY

It is an object of embodiments of the present disclosure to provide an easy to use device and method for analyzing a fluid sample.

It is an advantage of embodiments of the present disclosure that, at least for some actions, connecting the device to a separate fluid propagating element such as a pumping means can be avoided.

It is an advantage of embodiments of the present disclosure to provide compact devices for analyzing fluid samples as well as corresponding methods for analyzing fluid samples.

It is an advantage of embodiments of the present disclosure that low-cost devices for analyzing fluid samples can be provided, whereby such low-cost devices can, for example, be disposable.

This objective is accomplished by a method and device according to embodiments of the present disclosure.

According to an aspect of the disclosure, a fluid analyzing device is presented. The fluid analyzing device comprises: a sensing device for analyzing a fluid sample, the sensing device comprising: a microchip configured for sensing the fluid sample and a closed micro-fluidic component for propagating the fluid sample to the microchip. The fluid analyzing device also includes a vacuum compartment airtight connected to the sensing device and adapted for creating a suction force in the micro-fluidic component by opening the vacuum compartment, the suction force being suitable for propagating the fluid sample through the micro-fluidic component. Further the fluid analyzing device includes an inlet for providing the fluid sample to the micro-fluidic component. Hence, the micro-fluidic component is closed off from the inlet for providing the fluid sample. The sensing device may be defined as a medical device suitable for performing an analysis of a fluid sample, e.g., bodily fluid samples.

According to an embodiment of the disclosure, the vacuum compartment encloses a volume at lower pressure than atmospheric pressure, hence creating the suction force in the micro-fluidic component by opening the vacuum compartment. Vacuum thereby means that the pressure is lower than atmospheric pressure.

According to an embodiment of the disclosure, the fluid analyzing device further comprises a package comprising: the sensing device, the vacuum compartment, and the inlet. The sensing device and the vacuum compartment are encapsulated by the package. The inlet is located in the package, e.g., in a wall of the package, and is connected to the micro-fluidic component such that a fluid sample may be provided to the micro-fluidic component.

According to an embodiment of the disclosure, the vacuum compartment comprises a sacrificial element adapted to open the vacuum compartment towards the micro-fluidic component when the element is destructed.

According to an embodiment of the disclosure, the fluid analyzing device further comprises a movable structure for destructing the sacrificial element. The movable structure may be located in the package. Alternatively, the movable structure may be part of the vacuum compartment.

According to an embodiment of the disclosure, the movable structure is a movable puncture device adapted to destruct the sacrificial element when actuated from outside the package.

According to an embodiment of the disclosure, the sacrificial element comprises a heating resistor positioned such that the sacrificial element is destructed by heating.

According to an embodiment of the disclosure, the heating resistor is positioned in or on the sacrificial element. According to an embodiment of the disclosure, the heating resistor is positioned on a substrate comprising the micro-fluidic component. The heating resistor may be in contact with the sacrificial element.

According to an embodiment of the disclosure, the sacrificial element is solvent-dissolvable. The fluid analyzing device further comprises a solvent compartment containing a solvent. The solvent compartment is configured to release the solvent to the sacrificial element when the fluid sample is provided in the micro-fluidic component. By dissolving the sacrificial element by the released solvent, the vacuum compartment is opened.

According to an embodiment of the disclosure, the fluid analyzing device further comprises a fluid detector positioned to detect the fluid sample when provided in the micro-fluidic component. When the fluid sample is detected, the vacuum compartment is configured to open.

Additionally, the fluid analyzing device also may comprise features of the sensing device described below.

According to an aspect of the disclosure, a method for sensing a fluid sample is presented, comprising: providing a fluid analyzing device; providing a fluid sample to the micro-fluidic component via the inlet for providing the fluid sample to the micro-fluidic component; thereafter propagating the fluid sample through the micro-fluidic component by opening the vacuum compartment to create a pressure difference between the vacuum compartment and the micro-fluidic component; and performing sensing on the fluid sample using the sensing device.

According to an embodiment of the disclosure, the method for sensing a fluid sample further comprises detecting a fluid sample provided to the micro-fluidic component, and wherein the vacuum compartment is opened when the fluid sample is detected.

According to an aspect of the invention, the present disclosure relates to a sensing device for analyzing a fluid sample. The sensing device comprises: a fluidic substrate comprising a micro-fluidic component embedded in the fluidic substrate, where the fluidic substrate is configured to propagate a fluid sample via capillary force through the micro-fluidic component. The sensing device also includes a means connected to the micro-fluidic component for providing a fluid sample; a lid attached to the fluidic substrate thereby at least partly covering the fluidic substrate and at least partly closing the micro-fluidic component. The fluidic substrate is a silicon fluidic substrate and the lid is a microchip (e.g., a CMOS chip).

According to embodiments of the present disclosure, at least a part of the lid is in contact with the fluid sample when the fluid sample is present in the sensing device.

According to embodiments of the present disclosure, the lid comprises a transistor layer, the transistor layer being electrically connected at least one electrical component, the electrical component being at least one of the following: biosensing circuitry, electrodes for sensing purposes, electrodes for fluid manipulation purposes, circuitry for data communication purposes, circuitry for wireless data communication purposes, temperature sensors, heater electrodes for temperature control and fluid sensors and electrodes for fluidic viscosity control, imaging components, e.g., lensfree imaging components. These electrical components may be present on the lid, hence on the microchip. In an embodiment, the transistor layer and the electrical components are integrated in a single microchip.

According to embodiments of the present disclosure, the means for providing a fluid sample is a needle fabricated from a semiconductor, e.g., silicon, and comprises an inner fluidic channel connected to the micro-fluidic component. The needle is a protruding portion of the fluidic substrate and positioned to penetrate skin tissue when pressed against the skin tissue.

According to embodiments of the present disclosure, the fluidic substrate comprises a cut-out and the needle is positioned in the cut-out.

According to embodiments of the present disclosure, the fluidic substrate comprises a protection structure for protecting the needle, the protection structure being removably attached to the fluidic substrate.

According to embodiments of the present disclosure, the means for providing a fluid sample is an inlet. A sample drop may be inserted into the microfluidic component by means of capillary suction, or by other suitable means. The microfluidic component may comprise different fluidic compartments, for instance for multi-omic analysis. The different microfluidic compartments can have the same or different depths. The different microfluidic compartments may be separated by valves that may be actuated in any suitable way, for instance by fluidic forces or by electricity. Electrodes for actuation may be contained on the fluidic substrate or on the lid.

According to embodiments of the present disclosure, the fluidic substrate or the lid may further comprise at least one optical waveguide to allow optical excitation and sensing of the fluid sample when present in the sensing device. The fluidic substrate or the lid may also comprise filters for rejecting optical excitation from emission to measure a fluorescent signal. The fluidic substrate or the lid may comprise multispectral filters for measuring fluorescent signals with multiple colors. The fluidic substrate or the lid may comprise an optical waveguide and/or a pinhole to irradiate the sample for performing lensfree microscopy.

According to embodiments of the present disclosure, the fluidic substrate or the lid comprises at least one through-hole for application of a biochemical reagent to at least one region of the micro-fluidic component or to at least one region of the lid.

According to embodiments of the present disclosure, the lid is bonded to the fluidic substrate using a lithographically patterned polymer.

According to embodiments of the present disclosure, the sensing device may further comprise metal contacts electrically connected to the microchip for detecting electrical signals generated by the fluid and captured by measurement systems in the lid. According to embodiments of the present disclosure, the lid of the sensing device may further comprise CMOS active pixels for detecting optical signals from the fluid.

According to embodiments of the present disclosure, the fluidic substrate comprises a cut-out and the needle is positioned in the cut-out.

According to embodiments of the present disclosure, the fluidic substrate comprises a protection structure for protecting the needle, the protection structure being removably attached to the fluidic substrate.

According to embodiments of the present disclosure, the means for providing a fluid sample is an inlet. A sample drop may be inserted into the microfluidic component by means of capillary suction, or by other suitable means. The microfluidic component may comprise different fluidic compartments, for instance for multi-omic analysis. The different microfluidic compartments can have the same or different depths. The different microfluidic compartments may be separated by valves that may be actuated in any suitable way, for instance by fluidic forces or by electricity. Electrodes for actuation may be contained on the fluidic substrate or on the lid.

According to embodiments of the present disclosure, the fluidic substrate or the lid may further comprise at least one optical waveguide to allow optical excitation and sensing of the fluid sample when present in the sensing device. The fluidic substrate or the lid may also comprise filters for rejecting optical excitation from emission to measure a fluorescent signal. The fluidic substrate or the lid may comprise multispectral filters for measuring fluorescent signals with multiple colors. The fluidic substrate or the lid may comprise an optical waveguide and/or a pinhole to irradiate the sample for performing lensfree microscopy.

According to embodiments of the present disclosure, the fluidic substrate or the lid comprises at least one through-hole for application of a biochemical reagent to at least one region of the micro-fluidic component or to at least one region of the lid.

According to embodiments of the present disclosure, the lid is bonded to the fluidic substrate using a lithographically patterned polymer.

According to embodiments of the present disclosure, the sensing device may further comprise metal contacts electrically connected to the microchip for read-out of electrical signals generated by the fluid and captured by measurement systems in the lid. According to embodiments of the present disclosure, the lid of the sensing device may further comprise CMOS active pixels for readout of optical signals from the fluid.

According to embodiments of the present disclosure, at least part of the fluidic substrate and/or the lid is fabricated from a transparent material to allow optical inspection of a fluid sample in the micro-fluidic component.

According to embodiments of the present disclosure, the shape of the sensing device allows insertion into a mobile communication device.

According to an aspect, embodiments of the present disclosure relate to a method for fabricating a sensing device for analyzing a fluid sample. The method comprises: providing a fluidic substrate; providing a lid; attaching the fluidic substrate to the lid thereby at least partly close the fluidic substrate. The fluidic substrate is a semiconductor fluidic substrate and the lid is CMOS chip. The fluidic substrate is attached to the lid using a CMOS compatible bonding process.

According to embodiments of the present disclosure, providing a fluidic substrate may comprise: providing a semiconductor (e.g., silicon) substrate, providing a mask layer, for instance an oxide mask, patterning the mask layer so as to create fine structures in the oxide mask layer; providing a protection layer to protect the mask layer; patterning coarse structures; etching of the coarse structures; growing oxide for protecting the coarse structures; removing the protection layer and etch the fine structures; and removing the oxide.

According to embodiments of the present disclosure, providing a fluidic substrate may comprise providing a semiconductor substrate, providing a plurality of masks on top of one another, and using each mask for creating microfluidic structures of different depths.

In accordance with particular embodiments of the present disclosure, providing a fluidic substrate may comprise providing a semiconductor (e.g., silicon) substrate, providing a first oxide mask, patterning microfluidic structures, etching the substrate to single depth, providing a second oxide mask, patterning microfluidic structures, etching the substrate to a second depth, and, if required, repeating these steps for creating multiple depths of microfluidic structures.

According to particular embodiments, the fluidic substrate and the lid of a sensing device according to embodiments of the present disclosure may be integrated in a larger fluidic package, which may be made from different materials such as polymers, and which may contain larger fluidic structures, reagents, fluidic and electrical interfaces. The advantage thereof is that such system becomes more cost efficient.

According to embodiments of the present disclosure, surfaces of the fluidic substrate and the lid may be partially or fully coated to modify surface interactions of the substrate with the fluid sample.

According to an aspect of the disclosure, the present invention provides the use of the sensing device as described in the foregoing aspects to perform microscopy. Microscopy may be implemented by using the lid for detecting lensfree images according to the principles of digital holography.

The use of the sensing device as described may perform multi-omic analysis in which the fluidic substrate is used for performing multiple assays in multiple channels and chambers, and the CMOS lid is used to detect multiple signals from all assays. Those signals can combine multiple DNA, RNA, small molecule, cell signals from a same analyte.

In particular embodiments, the sensing device is used as a single use disposable device for analysis of a small amount of fluid.

According to an aspect of the disclosure, the data from the microchip may be sent to a smart handheld device, for instance using a wireless connection. The smart device can be used for processing, visualizing and/or transferring the data.

In embodiments of the present disclosure, the combined data gathered from a single same sample may be used in a software algorithm for calculating a parameter indicative of disease or of the wellbeing of an individual.

Example aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

BRIEF DESCRIPTION OF THE FIGURES

FIG. 11, FIG. 12, FIG. 13, FIG. 14, FIG. 15, FIG. 16, and FIG. 17 illustrate a method to fabricate a fluidic substrate for use in a sensing device, according to example embodiments.

FIG. 21 illustrates an embodiment of a CMOS chip for use in a sensing device, the CMOS chip comprising an I/O pad, according to an example embodiment.

FIG. 22 illustrates an embodiment of a CMOS chip for use in a sensing device, the CMOS chip comprising an I/O pad bonded to a fluidic substrate, according to an example embodiment.

Figure 1:
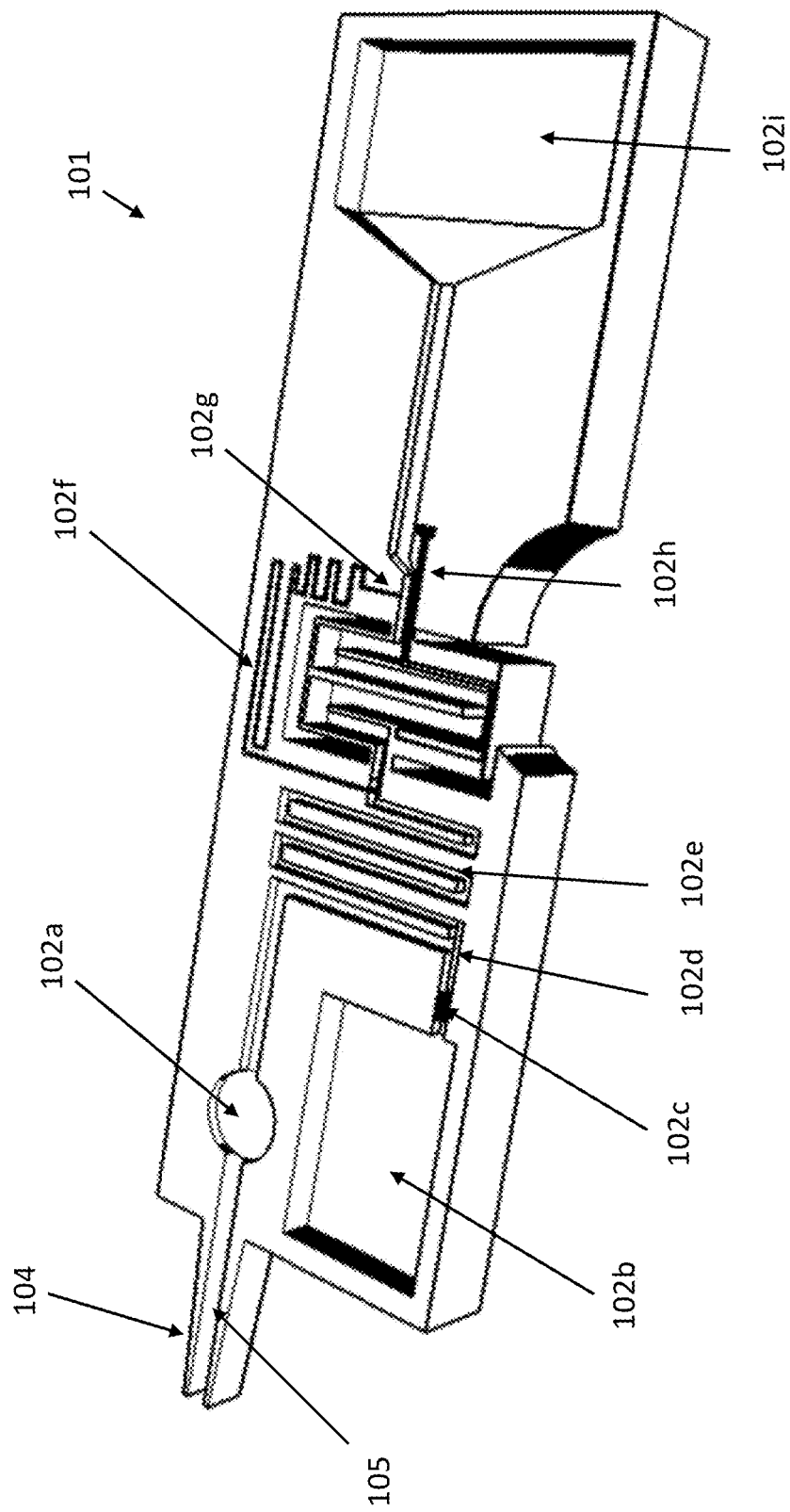
FIG. 1 illustrates a 3D view of an embodiment of a fluidic substrate, according to an example embodiment.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION

The present disclosure will be described with respect to particular embodiments and with reference to certain drawings but the invention is not limited thereto. The drawings described are only schematic and are non-limiting. In the drawings, the size of some of the elements may be exaggerated and not drawn on scale for illustrative purposes. The dimensions and the relative dimensions do not correspond to actual reductions to practice of the disclosure.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the disclosure described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present disclosure, the only relevant components of the device are A and B.

Reference throughout this specification to "one embodiment" or "an embodiment" means that a particular feature, structure or characteristic described in connection with the embodiment is included in at least one embodiment of the present disclosure. Thus, appearances of the phrases "in one embodiment" or "in an embodiment" in various places throughout this specification are not necessarily all referring to the same embodiment, but may be doing so. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the disclosure, various features of the disclosure are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the disclosure requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this disclosure.

Furthermore, while some embodiments described herein include some but not other features included in other embodiments, combinations of features of different embodiments are meant to be within the scope of the disclosure, and form different embodiments, as would be understood by those in the art. For example, in the following claims, any of the claimed embodiments can be used in any combination.

In the description provided herein, numerous specific details are set forth. However, it is understood that embodiments of the disclosure may be practiced without these specific details. In other instances, well-known methods, structures and techniques have not been shown in detail in order not to obscure an understanding of this description.

Where in embodiments of the present disclosure reference is made to an "I/O pad" or an "I/O contact", reference is made to a contact such as a metal contact allowing input and output of electrical signals of a micro-chip.

Where in embodiments of the present disclosure reference is made to "CMOS", reference is made to a Complementary Metal-Oxide Semiconductor.

Throughout the description reference is made to "fluid sample". This may refer to biological fluids including but not limited to blood, serum, urine, gastric and digestive juices, tears, saliva, stool, semen, and interstitial fluids derived from tumorous tissues.

Figure 34:
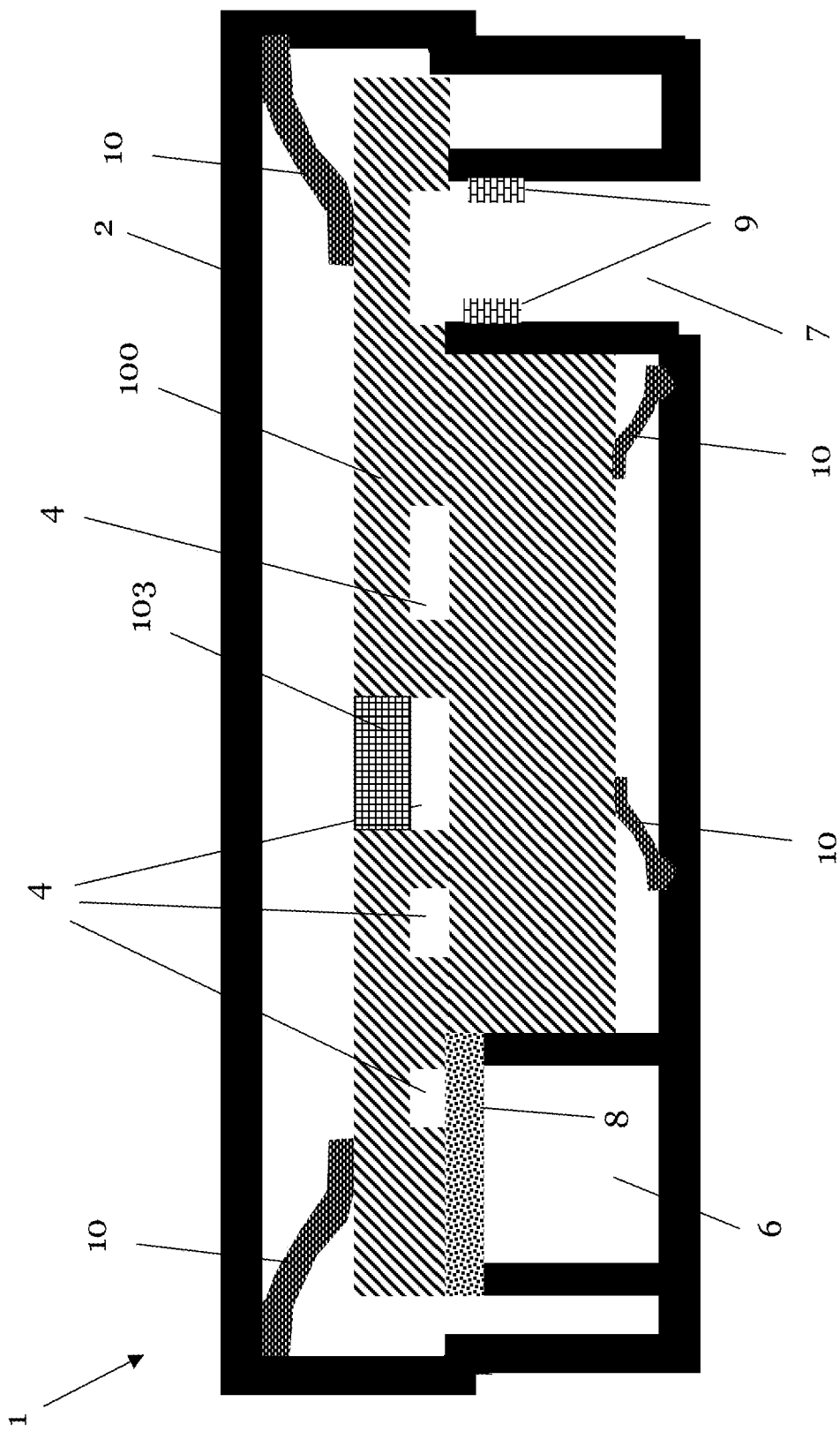
FIG. 34 illustrates a fluid analyzing device, according to an example embodiment.

According to an aspect of the disclosure, a fluid analyzing device 1 is presented (shown in FIG. 34). The fluid analyzing device 1 comprises a sensing device 100 which is adapted for analyzing a fluid sample. The sensing device 100 comprises a closed micro-fluidic component 4 for propagating the fluid sample to a microchip 103 which is disposed in the sensing device 100. The fluid analyzing device 1 further comprises an inlet for providing the fluid sample to the micro-fluidic component 4. Further, the fluid analyzing device 1 comprises a vacuum compartment 6 which is air-tight connected or attached to the micro-fluidic device 4. The micro-fluidic component 4 is embedded in a substrate (e.g., glass or silicon substrate) and thus is closed off from the inlet, and apart from the location where the vacuum compartment 6 is air tight connected to the sensing device 100. By opening the vacuum compartment 6 at the side attached to the sensing device 100, a suction force is created in the micro-fluidic component 4 which allows a fluid sample present in part of the micro-fluidic component 4 to propagate through the micro-fluidic component 4. By using a vacuum compartment to create the suction force, a cheap, power-free and reliable way of propagating the fluid sample is devised which makes it extremely suitable for use in single usage, disposable medical devices. (In this text and accompanying figures, the micro-fluidic component may be referred to with reference number "4" or with reference number "102").

According to an embodiment of the disclosure, the fluid analyzing device 1 further comprises a package 2 comprising the sensing device 100, the vacuum compartment 6 and the inlet 7. The package 2 encapsulates the sensing device 100, the vacuum compartment 6 and protects the fluid analyzing device 1 from the environment. For example, the package may be dust, water or shock proof. The package may be fabricated from a resilient material, e.g., a plastic. The inlet 7 in the package 2 is fluidically connected to the inlet of the micro-fluidic component 4. A fluid sample can be provided to the micro-fluidic component 4 via the inlet 7 of the package 2. If the micro-fluidic component 4 comprises multiple inlets, the package 2 may also comprise multiple corresponding inlets.

According to an embodiment of the disclosure, the micro-fluidic component 4 is fluidically connected on one end with the inlet 7 and fluidically connectable on the other end with the vacuum compartment 6, by opening the vacuum compartment 6. In some embodiments of the present invention, the vacuum compartment pressure is lower than atmospheric pressure. When the vacuum compartment 6 is opened, the pressure difference between the micro-fluidic component 4 and the vacuum compartment 6 forces a fluid sample which is provided at the inlet for the micro-fluidic component 4 to propagate through the micro-fluidic component 4, at least until the fluid sample reaches the microchip 103.

According to an embodiment of the disclosure, the vacuum compartment 6 is part of the sensing device. For example, the vacuum compartment may be a compartment located in the substrate that also comprises the micro-fluidic component 4. In such an embodiment, the compartment 6 may be a sealed cavity in the substrate which can be connected to the micro-fluidic component 4 by breaking the seal which seals the cavity. The seal may be a sacrificial element 8, such as a membrane, which can be destructed by suitable means, such as dissolution, by heating or by applying a force, for example an external pushing pressure.

According to an embodiment of the disclosure, to reduce cost and to minimize the usage of substrate material, the vacuum compartment 6 may be a separate component which is attached to the sensing device 100.

According to an embodiment of the disclosure, the vacuum compartment 6 may also be a part of the package 2, e.g., attached to the inside the package. For example, the vacuum compartment is attached to or is part of an inner wall of the package.

Different embodiments for the sacrificial element 8 may be provided. According to embodiments of the disclosure, the vacuum compartment 6 comprises a sacrificial element 8 which is adapted to open the vacuum compartment 6 towards the micro-fluidic component 102 when the element 8 is broken. The sacrificial element 8 is located such that when the element is broken, a suction force in the micro-fluidic component 102 can be created while maintaining the air-tight connection between the vacuum compartment 6 and the sensing device 100. The sacrificial element 8 may be a membrane, e.g., a sealing foil. The material and thickness of the sacrificial element is selected such that its resistance is sufficiently high thereby making it suitable for sealing the vacuum compartment 6.

According to an embodiment of the disclosure, the sacrificial element 8 comprises a heating element, such as for example a heating resistor, positioned such that the sacrificial element 8 is broken by heating when the heating element is electrically driven, thereby opening the vacuum compartment 6. Other variations of this method describing different method steps for breaking the sacrificial element 8 also correspond with embodiments of the present invention.

According to an embodiment of the disclosure, the heating element is positioned in or on the sacrificial element 8. According to an embodiment of the disclosure, the heating resistor is positioned on the sensing device 100, for example on the substrate which comprises the micro-fluidic component 4. The heating element may be in direct contact with the sacrificial element 8. In such an embodiment, the heating element is isolated from other parts of the substrate to minimize heat transfer to other components on the substrate. For example, the sensing device 100, e.g., the substrate comprising the micro-fluidic component 102, may comprise trenches located around the heating element to isolate the element from the rest of the sensing device 100.

The cross-section of a device according to an embodiment of the disclosure is illustrated in FIG. 34. A package 2 encapsulates a sensing device 100. This package is not essential. The sensing device 100 is fixed inside the package 2, e.g., via clamps. The sensing device 100 is positioned inside the package 2 such that a fluid sample introduced in the inlet 7 can enter the micro-fluidic component 4, e.g., via an inlet of the micro-fluidic component 4. A vacuum compartment 6 is attached to the sensing device 100. A microchip 103 is part of the sensing device 100 and is positioned such that it may perform direct sensing on a fluid sample inside the micro-fluidic component 4. The inlet 7 is connected to one end of the micro-fluidic component 4. The vacuum compartment 6 is connected to the other end of the micro-fluidic component 4. The microchip 103 is located along the micro-fluidic component 4, positioned in between the inlet 7 and the vacuum compartment 6 such that a fluid sample, introduced in the inlet 7 and propagated via a suction force created by opening the vacuum compartment, passes through or into the micro-chip. In some embodiments of the present disclosure, the microchip 103 may be disposed in a side of the channel of the micro-fluidic component 4, or it may be disposed in the lid.

According to an embodiment of the disclosure, the package 2 or the vacuum compartment 6 may comprise a movable structure 5 suitable for breaking the sacrificial element 8. The movable structure 5 may be a movable puncture device, positioned and adapted to break the sacrificial element 8 when actuated from outside the package 2 or from outside the vacuum compartment 6. The moveable puncture device may be integrated in a wall of the vacuum compartment 6 such that when the moveable puncture device is actuated, the air tight connection to the sensing device 100 is preserved. For preserving this air-tight connection, a diaphragm, e.g., fabricated from an elastic material, may be used which allows movement of the puncture device without causing a pressure loss in the vacuum compartment 6. Alternatively, a mechanical structure may be used which allows movement of the puncture device and which also preserves the air-tight connection. The moveable puncture device may comprise a needle which may be located inside the vacuum compartment 6. Hence, by moving the puncture device, the needle can be moved towards the sacrificial element 8 such that the sacrificial element 8 can be punctured when applying enough pressure on the moveable puncture device. The mechanical structure may comprise a spring which causes the mechanical structure to return to its initial position when the mechanical structure is not actuated.

Figure 35:
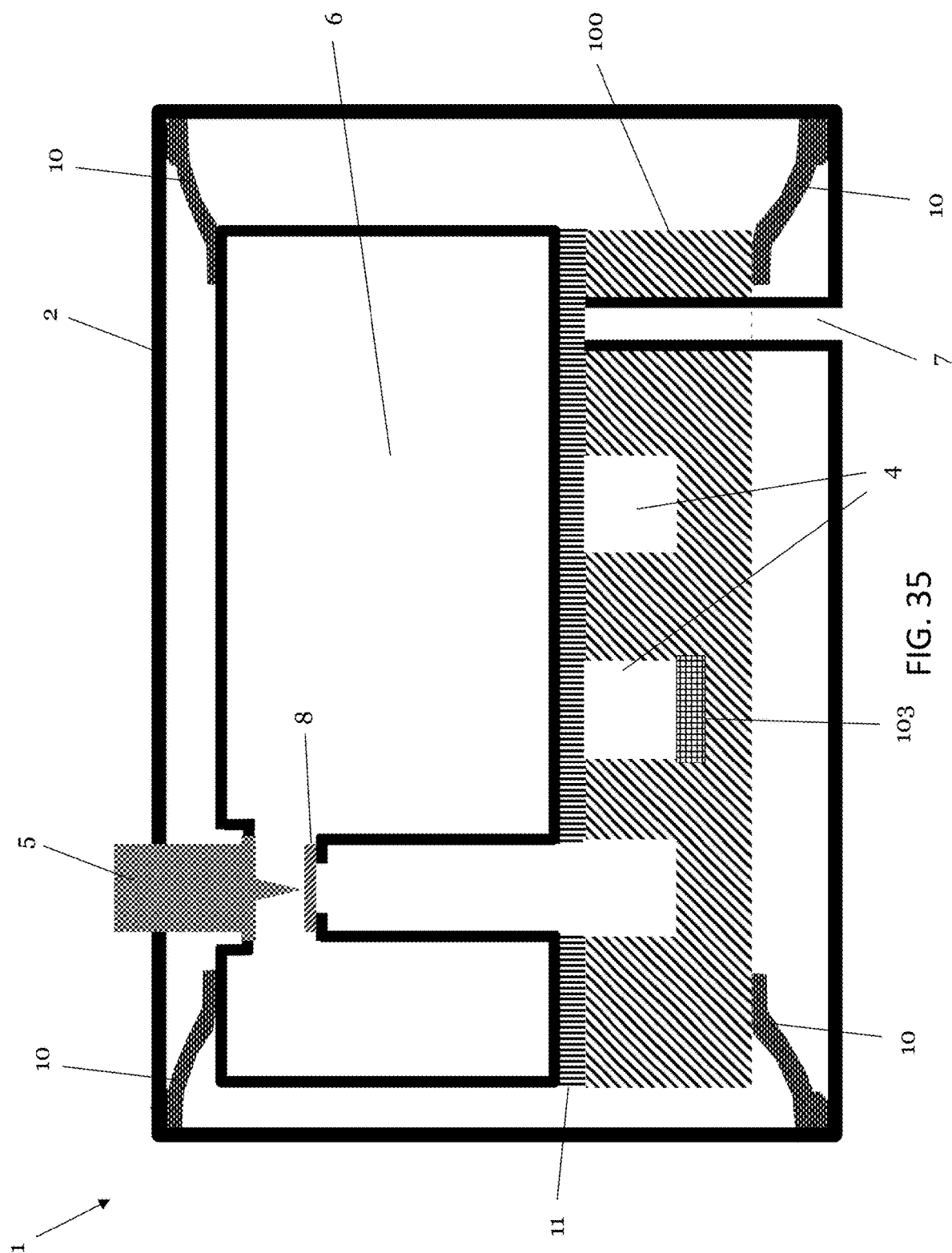
FIG. 35 illustrates another fluid analyzing device, according to an example embodiment.

Such an embodiment is illustrated in FIG. 35. A package 2 encapsulates a sensing device 100. The sensing device 100 is fixed inside the package 2, e.g., via clamps 10. The sensing device 100 is positioned inside the package 2 such that a fluid sample introduced in the inlet 7 can enter the micro-fluidic component 4. A vacuum compartment 6 is attached to the sensing device 100. In between the sensing device 100 and the vacuum compartment 6, a sealing layer 11 is present to bond the vacuum compartment 6 to the sensing device 100. The sealing layer may be a layer comprising a polymer. This sealing layer is optional. The sealing layer may be a gasket. The sealing layer is not present at the location where the vacuum compartment can be opened by breaking the sacrificial element 8. A microchip 103 is located in the sensing device 100 such that it may perform direct analysis on a fluid sample inside the micro-fluidic component 4. The inlet 7 is connected to one end of the micro-fluidic component 4. The vacuum compartment 6 is connected to the other end of the micro-fluidic component 4. The microchip 103 is located along the micro-fluidic component 4, in between the inlet 7 and the vacuum compartment 6 such that a fluid sample introduced in the inlet 7 and propagated via a suction force created by opening the vacuum compartment 6 passes the microchip 103 for sensing purposes. The vacuum compartment 6 can be opened by actuating the moveable puncture device 5 from outside the package 2. When the puncture device 5 is pushed by a user, the puncture device 5 approaches the sacrificial element 8 and eventually punctures the sacrificial element 8 thereby opening the vacuum compartment 6.

According to an embodiment of the disclosure, the sacrificial element 8 is solvent-dissolvable. The fluid analyzing device 1 further comprises a solvent compartment containing a solvent. The solvent compartment may be configured to release the solvent to the element 8 when the fluid sample is provided in the micro-fluidic component 4 thereby opening the vacuum compartment. The solvent compartment may also be configured to release the solvent to the element 8 by applying pressure to the vacuum compartment such that the solvent compartment breaks and releases its content on the sacrificial element 8. The solvent compartment may also be configured to release the solvent to the element 8 when it is electrically driven. For example, the fluid analyzing device 1 may comprise a switch or a button which generates an electrical signal to the element 8 causing the element 8 to break. The solvent compartment is positioned close to the sacrificial element 8 such that the sacrificial element 8 can be exposed to the solvent when the solvent compartment is opened. The solvent compartment may comprise a closed fluidic valve which can be opened when electrically driven. The solvent may be acetone. The sacrificial layer may be fabricated from a material dissolvable in acetone.

According to an embodiment of the disclosure, the fluid analyzing device 1 further comprises a fluid detector 9 which is positioned to detect the fluid sample when provided in the micro-fluidic component 4. The vacuum compartment 6 may be configured to open when the fluid sample is detected. The at least one fluid detector may be one or more electrical element, e.g., electrodes, configured to detect a fluid sample based on impedance or capacitance measurements. The electrodes may be positioned inside the inlet 7 of the package 2. The electrodes may be positioned on the sensing device 100, e.g., on an inner wall of the micro-fluidic component 4.

According to an embodiment of the disclosure, the fluid analyzing device 1 further comprises a switch or a push-button for activating the fluid analyzing device 1. The switch may be used to electrically connect the fluid analyzing device 1 to an on-board energy source, e.g., a battery. The switch may be adapted such that the sacrificial element 8 is electrically driven when the switch is actuated.

When electrically driving the sacrificial element 8, the vacuum compartment is opened. The switch may be adapted such that the sacrificial element 8 of the solvent compartment is electrically driven when the switch is actuated.

According to a method for operating the fluid analyzing device 1, a fluid sample is provided to the micro-fluidic component 4. Thereafter, the switch is actuated which causes the vacuum compartment to open thereby causing the fluid sample to propagate through the micro-fluidic component 4. The switch may for example act on a valve.

It will be understood that further features and advantages may correspond with one or more features of the sensing device described in further aspects below. Such one or more features may be applied mutatis mutandis in embodiments of the sensing device of the present aspect.

In an aspect of the disclosure, a method for sensing a fluid sample is presented. The method comprises providing a fluid analyzing device 1 according to an aspect of the disclosure. The method comprises providing a fluid sample to the micro-fluidic component 4; thereafter propagating the fluid sample through the micro-fluidic component 4 by opening the vacuum compartment 6 thereby creating a pressure difference between the vacuum compartment 6 and the micro-fluidic component 4; and performing sensing on the fluid sample using the sensing device 100.

According to an embodiment of the disclosure, the method further comprises detecting a fluid sample when it is provided to the micro-fluidic component 4, and wherein the vacuum compartment 6 is opened, or configured to open, when the fluid sample is detected.

Figure 25:
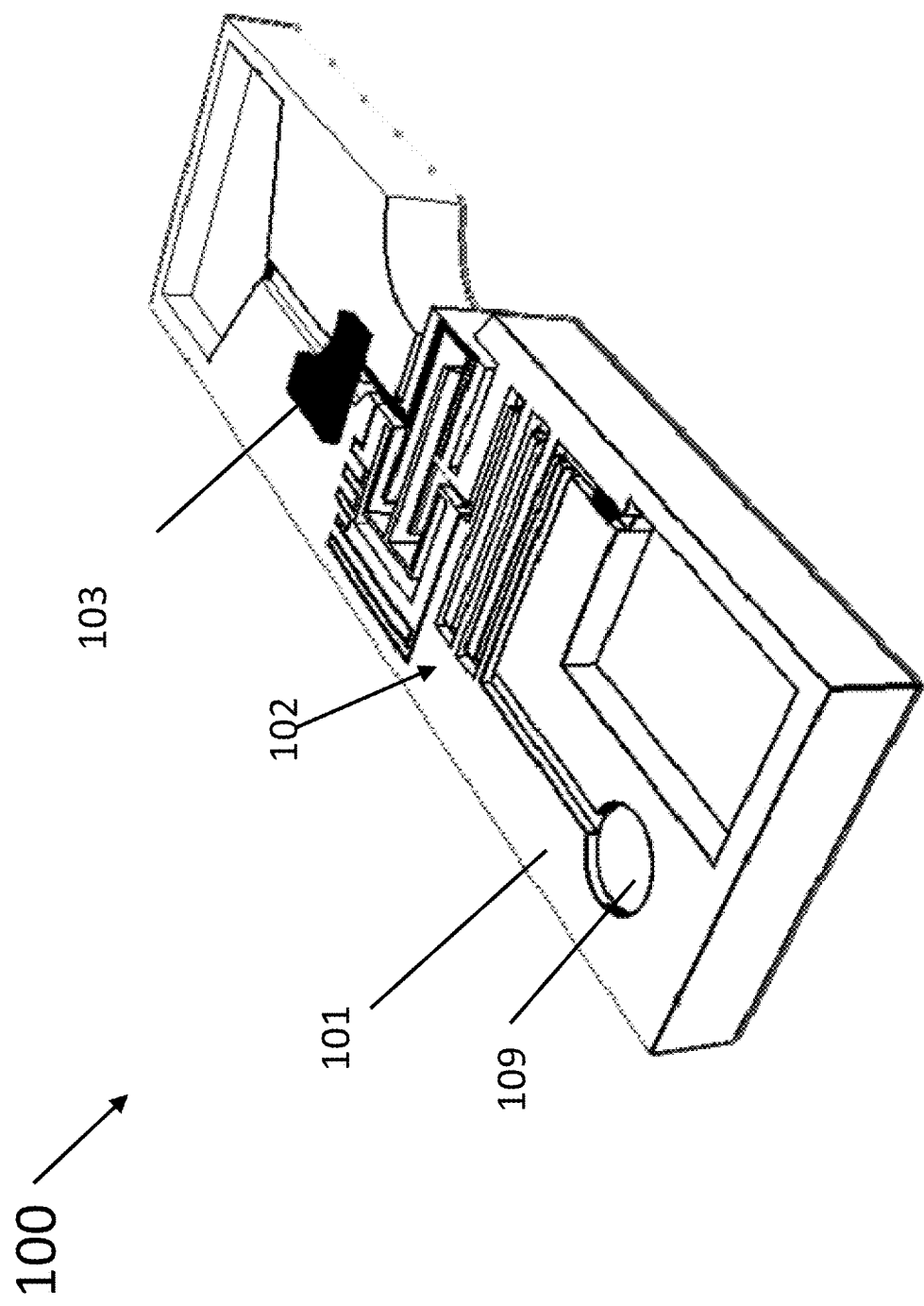
FIG. 25 illustrates a 3D view of a sensing device, according to an example embodiment.
Figure 26:
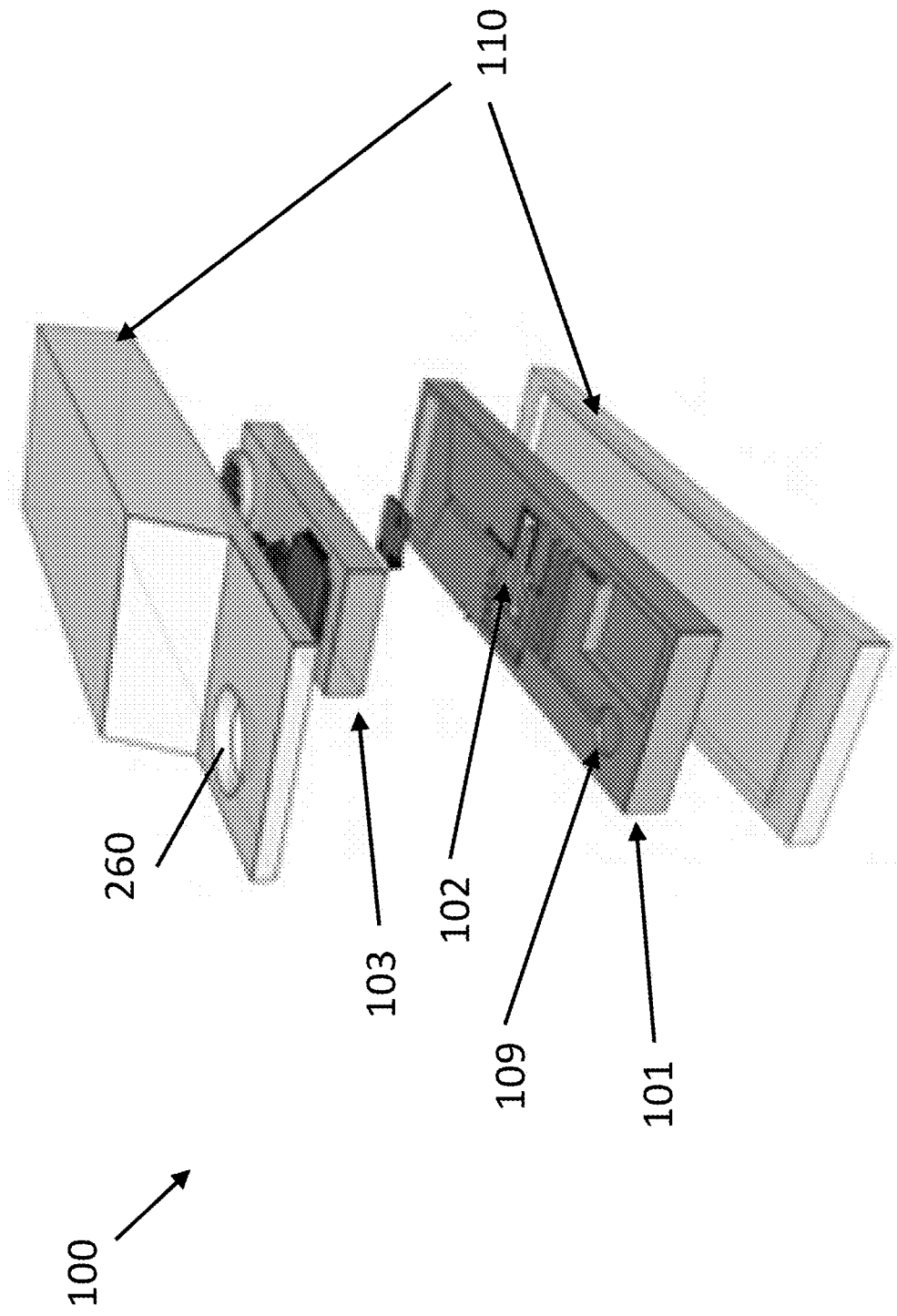
FIG. 26 illustrates a 3D view of a wireless stand-alone sensing device, according to an example embodiment.

An aspect of the disclosure relates to a sensing device 100 for analyzing a fluid sample, as for instance illustrated in FIGS. 25 and 26. The sensing device 100 comprises: an exemplary fluidic substrate 101 and a lid attached to the fluidic substrate 101 at least partly covering the substrate 101. The fluidic substrate 101 comprises a micro-fluidic component 102 (in the present example illustrated by a plurality of microfluidic components such as a sample pad 102a (i.e., an inlet), a reagent storage 102b, a one-time usage hermetic valve 102c, a first trigger valve 102d, a mixer 102e, a delay line 102f, a second trigger valve 102g, an a heater 102h and a wick 102i) embedded in the fluidic substrate 101 configured to propagate a fluid sample via capillary force through the micro-fluidic component 102; and a means connected to the micro-fluidic component 102 for providing a fluid sample. The lid, by at least partly covering the substrate 101, at least partly closes the micro-fluidic component 102. In embodiments of the present disclosure, the fluidic substrate 101 is a silicon fluidic substrate; and the lid is a CMOS chip. The lid functions as a cover for the fluidic substrate 101 wherein the lid fully or partly closes the micro-fluidic component 102. FIG. 25 illustrates an embodiment of the present disclosure wherein the lid partly covers the fluidic substrate 101. The lid may fully or also partially cover the fluidic substrate 101. When the means for providing a fluid sample is an inlet 109 (as illustrated in FIG. 26), for instance a sample pad 102a, the lid may partially cover the fluidic substrate 101, allowing a user to access the inlet 109 to deposit a fluid sample. When the fluid enters in contact with a fluid detector, or by a switching action, the vacuum chamber may open and suck the liquid into the micro-fluidic channels of the micro-fluidic component 102.

As the fluidic substrate 101 may be a silicon substrate and the lid may comprise a CMOS chip, both can be manufactured using mass production compatible silicon process technologies. As an additional advantage, cheap CMOS packaging techniques may be used to bond the silicon substrate to the CMOS chip. This reduces the total cost of the sensing device and allows it to be used as a disposable device and produced in high volume. Alternatively, the fluidic substrate 101 is a glass substrate.

FIG. 1 illustrates a 3D view of an example embodiment of a fluidic substrate 101.

Figure 3:
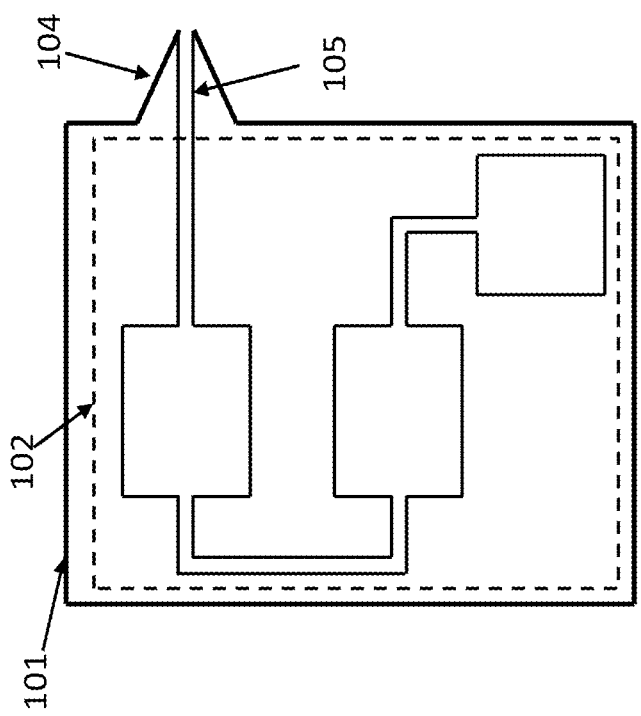
FIG. 3 illustrates a top view of a fluidic substrate used in the sensing device of FIG. 2, according to an example embodiment.
Figure 2:
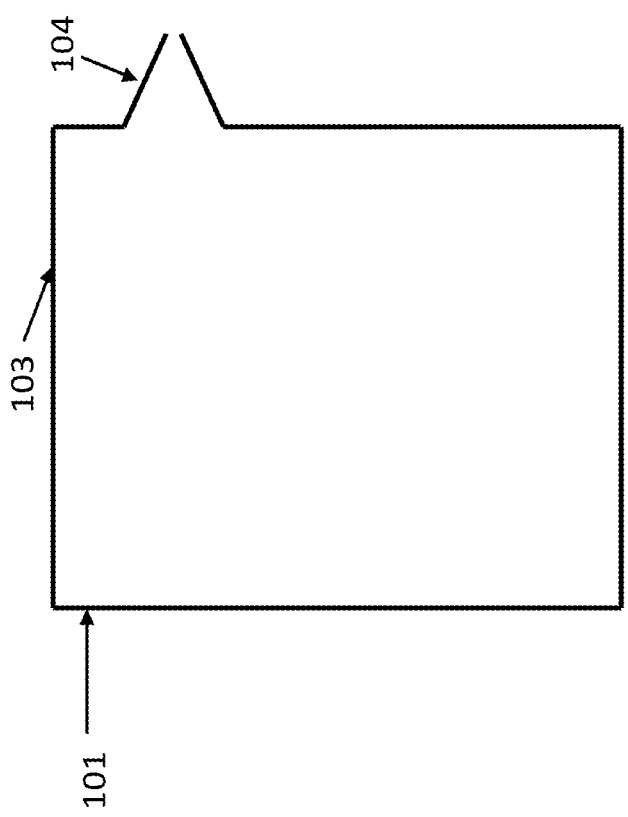
FIG. 2 illustrates a top view of a first embodiment of a sensing device for analyzing a fluid sample, according to an example embodiment.
Figure 4:
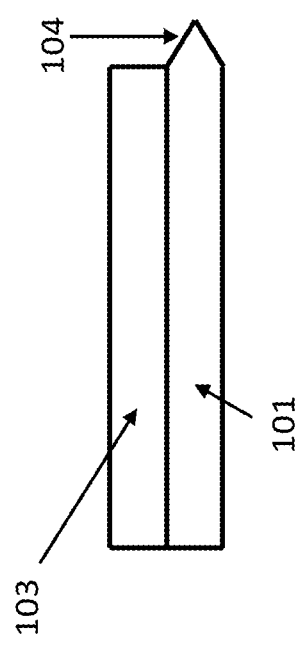
FIG. 4 illustrates a side view of the sensing device of FIG. 2, according to an example embodiment.

A top view of an embodiment of the sensing device 100 is illustrated in FIG. 2, the fluidic substrate 101 and the lid are attached to one another. A top view of an exemplary fluidic substrate 101 used in the sensing device of FIG. 2 is illustrated in FIG. 3. A side view of an embodiment of the sensing device 100 of FIG. 2 where the fluidic substrate 101 is attached to the lid comprising a microchip 103 is illustrated in FIG. 4.

A sensing device 100 according to embodiments of the present disclosure comprises a fluidic substrate 101 which is attached or bonded to a lid. The fluidic substrate 101 comprises a micro-fluidic component 102. The micro-fluidic component 102 may comprise micro-fluidic channels, micro-reactors or other micro-fluidic parts/structures which are interconnected to allow a fluid sample to propagate through the complete micro-fluidic component 102. Additionally and/or alternatively, the micro-fluidic component 102 may comprise a plurality of micro-pillars or microstructures at regular or irregular distances to allow filtering and separation, to act as valves, to allow mixing of a fluid sample during capillary flow.

Figure 27:
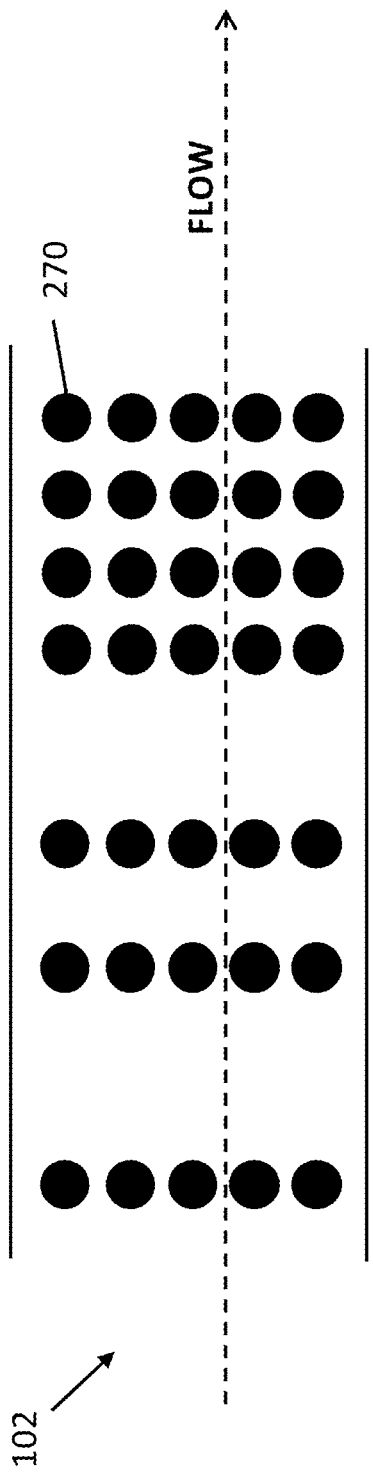
FIG. 27 illustrates a top view of a part of a micro-fluidic component for use in a sensing device, the micro-fluidic component comprising micro-pillars, according to an example embodiment.
Figure 28:
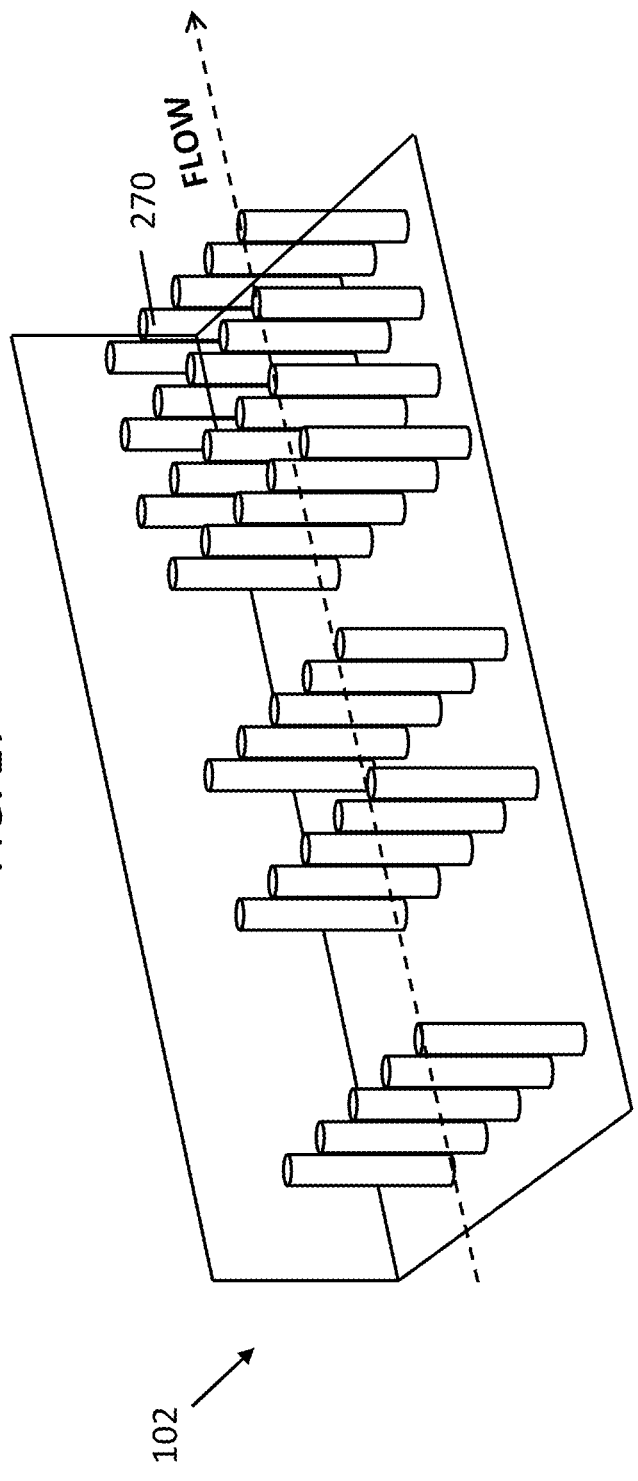
FIG. 28 illustrates a 3D view of a part of the micro-fluidic component of FIG. 27, according to an example embodiment.
Figure 29:
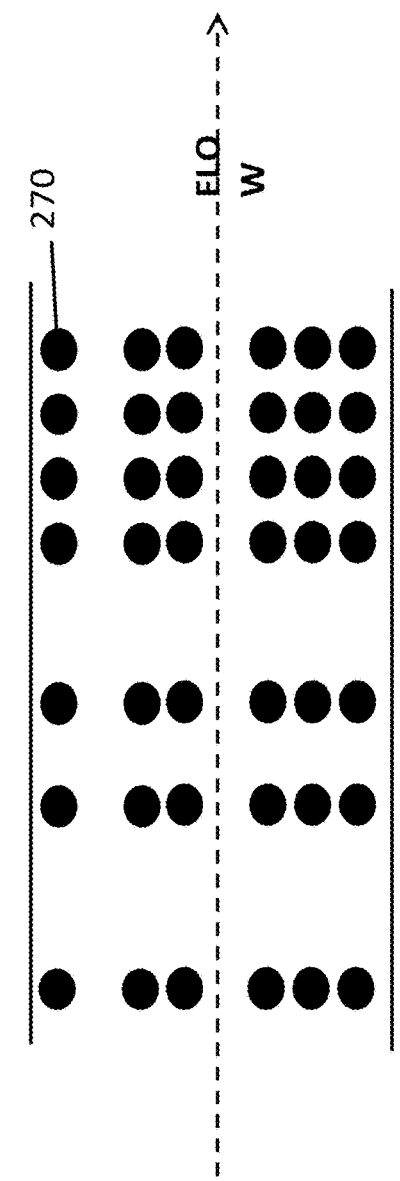
FIG. 29 illustrates a top view of a part of a second embodiment of a micro-fluidic component for use in a sensing device, the micro-fluidic component comprising micro-pillars, according to an example embodiment.
Figure 30:
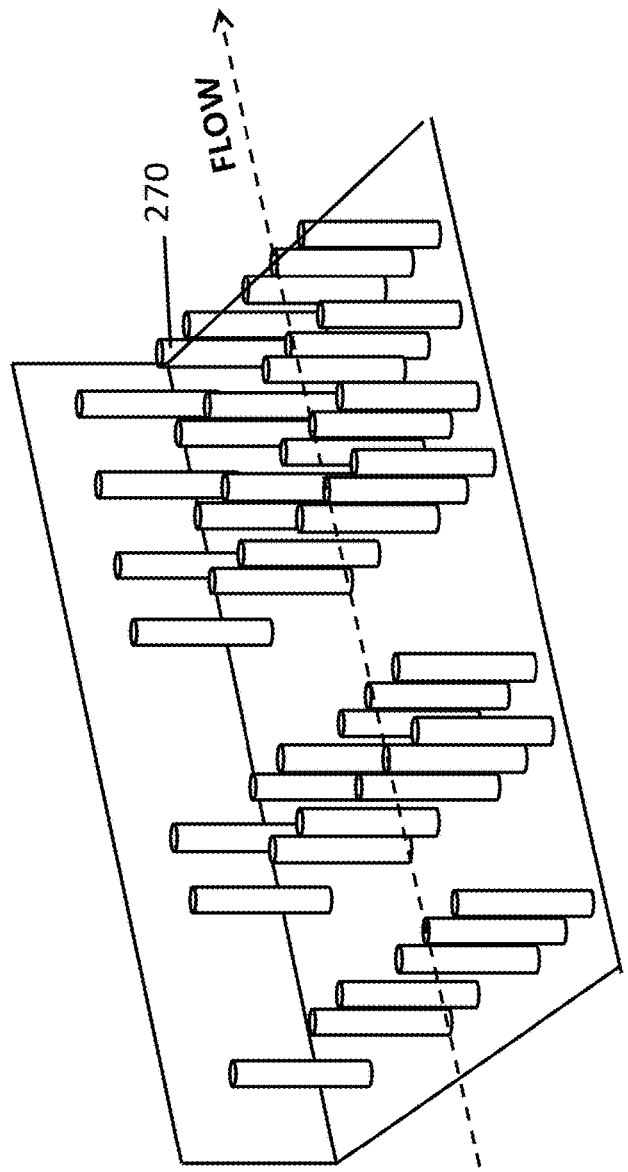
FIG. 30 illustrates a 3D view of a part of the micro-fluidic component of FIG. 29, according to an example embodiment.

FIG. 27 illustrates a top view of a part of micro-fluidic component 102 comprising micro-pillars 270 to allow filtering and separation, valving, mixing of a fluid sample during capillary flow. FIG. 28 illustrates a 3D view of the open micro-fluidic component 102 of FIG. 27 comprising micro-pillars 270. The micro-pillars 270 in FIG. 27 and FIG. 28 are positioned as to form a gradient. This gradient is advantageous to filter out larger particles in a first part of the micro-fluidic component 102 and to filter out smaller particles in a second part of the micro-fluidic component 102. FIG. 29 and FIG. 30 illustrate another embodiment of a gradient of micro-pillars 270 in the micro-fluidic component 102. The micro-fluidic component 102 may be configured to create a capillary action to propagate a fluid sample through the sensing device 100. The dimensions of the micro-fluidic component 102 may be adapted to create a capillary action in the micro-fluidic component 102 when a fluid sample is present. For example, dimensions and distance between micro-pillars 270 in the micro-fluidic component 102 may be configured to create a capillary action in the micro-fluidic component 102. As an advantage, in embodiments of the present disclosure, the sensing device 100 does not need additional active components (e.g., an active pump) to propagate a fluid sample through the sensing device 100. Thus, the complexity of the sensing device 100 is reduced compared to other implementations, which reduces fabrication cost and power consumption. As the costs to fabricate are low, the sensing device may be used as a disposable fluid analysis device.

It is an advantage of embodiments of the present disclosure that precise control over the flow of a fluid sample in the micro-fluidic component 102 may be achieved by, for example, correctly dimensioning (i) the micro-fluidic channels and/or micro-pillar sizes and (ii) distances which are present in the micro-fluidic component 102. Lithographic patterning may be used to fabricate the micro-fluidic component 102 in the fluidic substrate 101. It is an advantage that the lithographic patterning of micro-pillars and micro-fluidic channels of the micro-fluidic component 102 allows to accurately control the dimensions, size, and shape of the micro-pillars and micro-fluidic channels, thereby precisely controlling the capillary flow. This precise control over the dimensions, achievable via lithographic processes, presents an advantage in achieving more controllable lateral flow than the state of the art lateral flow test strips, which are made from porous paper with uncontrolled lateral flow. By varying the dimensions over the length of the sensing device it is possible to slow down and/or to increase the speed of the flow of a fluid sample where desired. This allows implementation biochemical reactions that are more complex than the simple flow used in existing lateral flow immunoassay tests. The combination with the functions implemented in the CMOS chip bonded as a lid onto the fluidic substrate 101 further adds temperature control, electrical fluid actuation and valving, integrated biosensing and measurement where needed. Therefore it becomes possible to implement complex assays, including DNA/RNA assays, proteins, small molecules and cells and combinations thereof in one integrated capillary system. Moreover, the implementation of capillary flow in silicon with controlled lateral flow and with control over the temperature and flow rate results in more accurate point of care test results.

According to some embodiments, a vacuum compartment for sucking the fluid sample through the micro-fluidic component may be provided. This may be provided alternative to or in addition to the capillary system or pillar structures as described above. To use the sensing device, a user may deposit a drop of fluid, e.g., a bodily fluid such as blood or saliva on the inlet 109 of the sensing device. When the fluid is to be introduced to the micro-fluidic component, the vacuum compartment is opened and the underpressure induces propagation of fluid, e.g., bodily fluid, through the micro-fluidic component 102. The propagation may be further enhanced by capillary forces.

FIG. 26 illustrates an exploded view of a fluid analyzing device 1 according to embodiments of the present disclosure, comprising a fluidic substrate 101 comprising an inlet 109 and a micro-fluidic component 102, a lid comprising a microchip 103, and a package 110. The package 110 may comprise a base and a top which can be assembled together to package the fluidic substrate 101 and the lid, thus protecting these from environmental influences such as dust. In some embodiments, the lid may be part of the top of the package 110. The package may comprise a through-hole 260 for depositing a fluid sample on an inlet 109 of the fluidic substrate 101. When all parts are assembled, the sensing device 100 may function as a stand-alone wireless device for analyzing a fluid sample. The microfluidic component 102 in FIGS. 25 and 26 may comprise a microchip 103 and a vacuum compartment for creating a negative pressure and bring fluids into the channels towards the microchip, according to embodiments of the present disclosure.

In FIG. 1, a 3D view of an exemplary fluidic substrate according to some embodiments of the present disclosure is shown.

In embodiments of the present disclosure the fluidic substrate 101 comprises a means, for providing a fluid sample, which is connected to the micro-fluidic component 102.

The lid functions as a cover for the fluidic substrate 101 wherein the lid fully or partly closes the micro-fluidic component 102. FIG. 25 illustrates an embodiment of the present disclosure wherein the microchip 103, which may be part of a lid, partly covers the fluidic substrate 101. The micro-fluidic component 102 may be a micro-fluidic component 102 in the fluidic substrate 101. According to alternative embodiments of the present disclosure, the dimensions of the microchip 103 may be identical to the dimensions of the fluidic substrate 101. The microchip 103 may fully or also partially cover the fluidic substrate 101. When the means for providing a fluid sample is an inlet 109 (as illustrated in FIG. 26), for instance a sample pad 102a, the microchip 103 may partially cover the fluidic substrate 101, allowing a user to access the inlet 109 to deposit a fluid sample.

According to embodiments of the present disclosure, the sensing device 100 may further comprise one or more electrodes which are placed on the micro-fluidic component 102 of the fluidic substrate 101. These electrodes may be biocompatible electrodes. The electrodes may be electrically connected to the lid comprising a microchip 103 and are allowed to interact with a fluid sample in the micro-fluidic component 102 of the sensing device 100 as they may be in direct contact with a fluid sample in the micro-fluidic component 102. While the lid itself may comprise electrodes, it is advantageous to separate the electrodes from the lid to allow the lid to be smaller, which reduces costs.

According to embodiments of the present disclosure, the micro-fluidic component 102 may comprise a capillary pump.

According to embodiments of the present disclosure, the means for providing a fluid sample may be an integrated needle 104, for instance fabricated from silicon, and comprising an inner fluidic channel 105 connected to the micro-fluidic component 102. The needle 104 may be a protruding portion of the fluidic substrate 101 and may be positioned so as to penetrate skin tissue when pressed against that skin tissue.

The fluidic substrate 101 and the needle 104 may be fabricated from a single piece of semiconductor. This simplifies the fabrication of the sensing device 100 according to embodiments of the present disclosure, as separate steps to attach a needle 104 to the fluidic substrate 101 are not required. Also, standard CMOS processing techniques may be used to fabricate the needle 104. Preferably the needle 104 is a sharp needle which allows skin tissue to be penetrated. The fluidic substrate 101 and the needle 104 may be both fabricated from the same or different semiconductors. For example, a needle fabricated from silicon has the advantage of allowing the needle 104 to be very sharp, which eases the penetration of the needle 104 in skin tissue. Further, the strength of the silicon allows skin tissue to be firmly pressed against the needle 104, allowing penetration of skin tissue without bending or breaking the needle 104.

According to embodiments of the present disclosure, the needle 104 may be positioned in a horizontal plane of the fluidic substrate 101 wherein the needle 104 is positioned on a sidewall of the fluidic substrate 101. The needle 104 may be a protruding portion of a sidewall of the fluidic substrate 101. According to a different embodiment, the needle 104 may be positioned on a horizontal plane of the fluidic substrate 101 wherein the needle is positioned perpendicular on a major surface of the fluidic substrate 101. According to embodiments of the present disclosure, the needle 104 may feature an open channel connected to the micro-fluidic component 102, wherein, in use, the skin tissue functions as a side-wall of the needle 104 when skin tissue is penetrated.

The sensing device 100 according to embodiments of the present disclosure may be used by pressing skin tissue of a user against the needle 104. When sufficient force is used, the needle 104 penetrates the skin tissue, allowing blood to enter the inner fluidic channel 105 of the needle 104. The needle 104 comprises a tip which is open to allow a fluid sample to enter the inner fluidic channel 105. When the needle is sharp with a small outer diameter (preferably smaller than 200 um) the penetration of the skin tissue will not cause any discomfort to the user. As the inner fluidic channel 105 of the needle 104 is connected to the micro-fluidic component 102 of the fluidic substrate 101, blood may enter the micro-fluidic component 102. Due to capillary force and the suction provided by the aperture of the vacuum compartment, blood will propagate through the micro-fluidic component 102.

FIG. 1 illustrates an embodiment of the fluidic substrate 101 with an integrated needle 104 (as part of the fluidic substrate 101), the needle having an inner fluidic channel 105 connected to a micro-fluidic component 102. The micro-fluidic component 102 may comprise: a sample pad 102a (which may have the functions of an inlet in some embodiments of the present disclosure), a reagent storage 102b, a one-time usage hermetic valve 102c, a first trigger valve 102d, a mixer 102e, a delay line 102f, a second trigger valve 102g, an heater 102h and a wick 102i. The lid (e.g., microchip 103 of FIG. 2) may function as a cover to close some or all fluidic components.

According to embodiments of the present disclosure, the fluidic substrate 101 may comprise a cut-out 106 wherein the needle 104 is positioned in the cut-out 106. The cut-out 106 is a removed part of the fluidic substrate 101 to offer mechanical protection for the needle 104 which resides in the cut-out 106.

Figure 6:
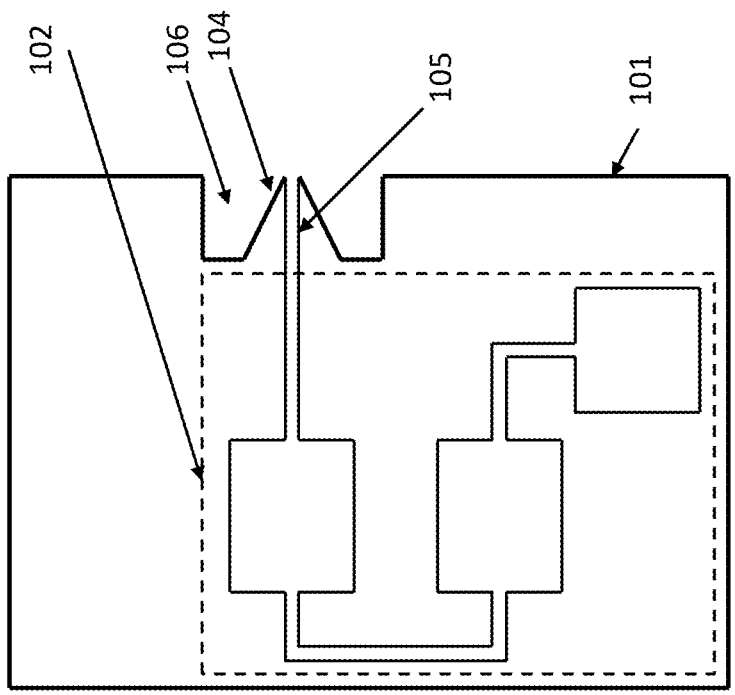
FIG. 6 illustrates a top view of an embodiment of a fluidic substrate featuring a cut-out for a needle, for use in the sensing device of FIG. 5, according to an example embodiment.
Figure 5:
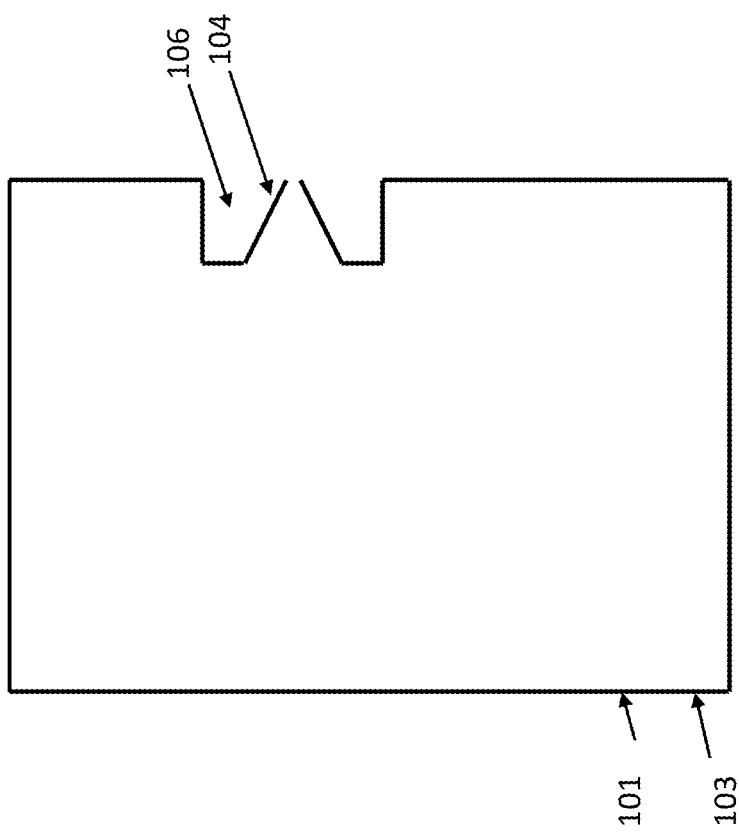
FIG. 5 illustrates a top view of a sensing device, for analyzing a fluid, featuring a cut-out for a needle, according to an example embodiment.
Figure 7:
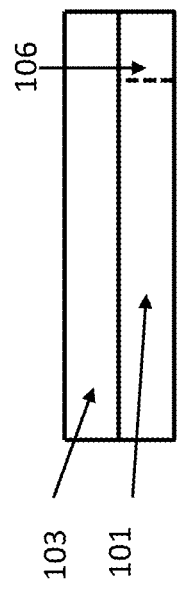
FIG. 7 illustrates a side view of the sensing device of FIG. 5, according to an example embodiment.

FIG. 5 illustrates a top view of an embodiment of the present disclosure wherein the lid comprising a microchip 103 is bonded to the fluidic substrate 101. FIG. 6 illustrates a top view of an exemplary fluidic substrate 101 of an embodiment of the present disclosure. FIG. 7 illustrates a side view of an embodiment of the present disclosure wherein the lid comprising a microchip 103 is bonded to the fluidic substrate 101.

As illustrated in FIG. 5, FIG. 6 and FIG. 7, the needle 104 is located in a cut-out 106 of the fluidic substrate 101. The cut-out 106 protects the needle 104 from breaking, for example, when the sensing device 100 is inserted in a slot of an external device (e.g., a mobile device such as a smartphone) for readout. The sidewall of the fluidic substrate 101 may feature the cut-out 106. The needle 104 may be positioned in the cut-out 106 to allow a user to penetrate skin tissue when pressed firmly against the cut-out 106. As a further advantage, during fabrication, the needle 104 may be fabricated while fabricating the cut-out 106. As a result, less material is wasted as only the material for the cut-out 106, excluding the material for the needle 104, needs to be removed. The cut-out 106 and needle 104 may be fabricated using standard semiconductor processing techniques.

Figure 9:
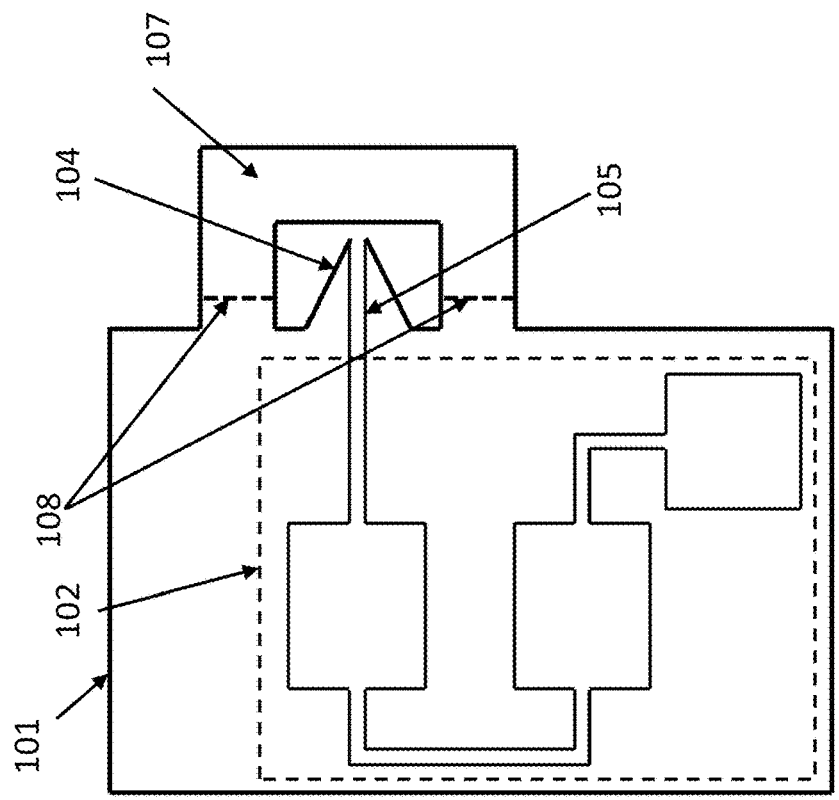
FIG. 9 illustrates a top view of an embodiment of a fluidic substrate featuring a protection structure for a needle, for use in the sensing device of FIG. 8, according to an example embodiment.
Figure 8:
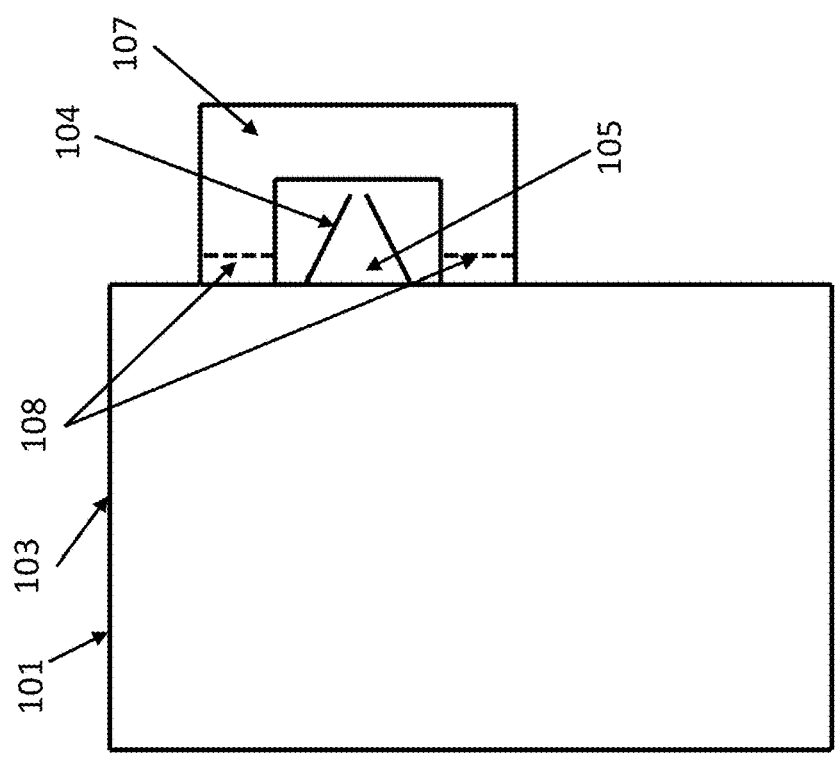
FIG. 8 illustrates a top view of a sensing device, for analyzing a fluid sample, featuring a protection structure for a needle, according to an example embodiment.
Figure 10:
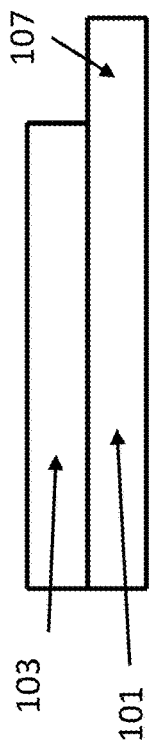
FIG. 10 illustrates a side view of the sensing device of FIG. 8, according to an example embodiment.

According to embodiments of the present disclosure shown in FIG. 8, FIG. 9 and FIG. 10, the fluidic substrate 101 may comprise a protection structure 107 for protecting the needle 104, removably attached to the fluidic substrate 101. According to embodiments of the present disclosure, the protection structure 107 may be attached to the fluidic substrate 101 via at least one anchoring mechanism 108. The protection structure 107 may be detached by breaking the at least one anchoring mechanism 108. The protection structure 107 may be part of the fluidic substrate 101 where the anchoring mechanism 108 may be a groove in the fluidic substrate 101 to allow breaking of the protection structure 107 at the groove. FIG. 8 is a top view of such an embodiment of a sensing device 100. As can be seen in FIG. 9 (illustrated is a top view of an exemplary embodiment of a fluidic substrate 101 for use in a sensing device according to embodiments of the present disclosure, such as a sensing device as illustrated in FIG. 8), the protection structure 107 is part of the fluidic substrate 101 and features two anchoring mechanisms 108 which allow detaching of the protection structure 107 from the fluidic substrate 101. FIG. 10 illustrates a side view of the sensing device 100 of FIG. 8 or FIG. 9.

According to embodiments of the present disclosure shown in FIG. 25 and FIG. 26, the means for providing a fluid sample may be an inlet 109. The inlet 109 may be an indentation in the fluidic substrate 101 which is connected to the micro-fluidic component 102 by a fluidic channel. To use the sensing device, a user may deposit a drop of bodily fluid such as blood or saliva on the inlet 109 of the sensing device. Due to capillary force, the bodily fluid will propagate through the micro-fluidic component 102.

FIG. 26 illustrates a de-assembled sensing device 100 according to embodiments of the present disclosure, comprising a fluidic substrate 101 comprising an inlet 109 and a microfluidic component 102, a lid comprising a microchip 103, and a package 110. The package 110 may comprise a base and a top which can be assembled together to package the fluidic substrate 101 and the lid comprising a microchip 103, thus protecting these from environmental influences such as dust. The package may comprise a through-hole 260 for depositing a fluid sample on an inlet 109 of the fluidic substrate 101. When all parts are assembled, the sensing device 100 may function as a stand-alone wireless device for analyzing a fluid sample.

According to embodiments of the present disclosure, at least a part of the microchip 103 may be in contact with the fluid sample when the fluid sample is present in the sensing device 100. When the microchip 103 is a CMOS chip, electronic circuitry present on a surface of the chip may be in direct contact with the fluid sample when the microchip 103 is functioning as a side-wall of a micro-fluidic component 102 in the fluidic substrate 101. In this case, the side of the chip comprising electronic circuitry may be bonded to a micro-fluidic component 102 of the fluidic substrate 101 wherein the electronic circuitry is aligned with parts of the micro-fluidic component 102 where interaction with a fluid sample is desired. As an advantage, this may improve the interaction between the electronic circuitry and the fluid sample.

According to embodiments of the present disclosure, the lid 3 may comprise bonding layers to enable bonding of the lid to the fluidic substrate 101.

According to embodiments of the present disclosure, a first side of the fluidic substrate 101 comprising a microfluidic component 102 may be bonded to a first side of the microchip 103 comprising at least one electrical component.

According to an embodiment, the lid may comprise a microchip 103 comprising a transistor layer, the transistor layer being electrically connected at least one electrical component, the electrical component being at least one of the following: biosensing circuitry, electrodes for sensing purposes, electrodes for fluid manipulation purposes, circuitry for data communication purposes, circuitry for wireless data communication purposes, temperature sensors, heater electrodes for temperature control or temperature cycling, and fluid sensors and electrodes for fluidic viscosity control. The circuitry for wireless data communication may comprise provisions for communication via a Bluetooth radio or a WiFi module for wirelessly transmitting data from electronic circuitry in the lid 3. As an advantage, the sensing device 100 may communicate with an external device, such as a mobile device, which may be used to further process the data.

According to FIG. 18, FIG. 19, FIG. 21 and FIG. 22, the CMOS chip may comprise a silicon substrate 111, a transistor layer 112, at least one electrical component electrically connected to the transistor layer 112, and at least one bonding layer 115. The at least one electrical component may be biosensing circuitry, electrodes for sensing purposes, electrodes for fluid manipulation purposes, circuitry for data communication purposes, circuitry for wireless data communication purposes, temperature sensors, heater electrodes for temperature control, and fluid sensors and electrodes for fluidic viscosity control.

Figure 18:
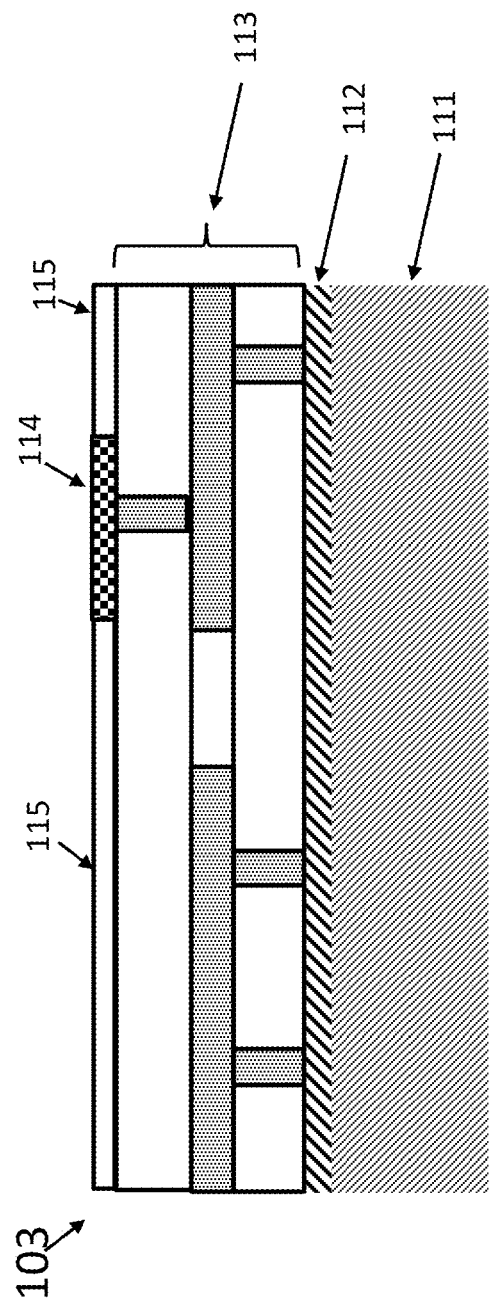
FIG. 18 illustrates an embodiment of a CMOS chip for use in a sensing device, according to an example embodiment.

A particular embodiment of a microchip 103 according to embodiments of the present disclosure is illustrated in FIG. 18. In this embodiment, the microchip 103 comprises a silicon substrate 111. Atop the silicon substrate 111 a transistor layer 112 may be present. Atop the transistor layer 112 an interconnection layer 113 may be present. Atop the transistor layer 112, at least one electrical component may be present electrically connected to the transistor layer 112 via the interconnection layer 113. The interconnection layer 113 may comprise a plurality of metal layers. According to embodiments of the present disclosure, atop the transistor layer 112, a bonding layer 115 and at least one electrode 114 may be present. The electrode 114 may be electrically connected to the transistor layer via the interconnection layer 113.

According to embodiments of the present disclosure, the at least one electrical component may be a biocompatible electrode which is fluid corrosion free and chemically inert. According to a specific embodiment, the at least one electrode 114 is TiN electrode.

According to embodiments of the present disclosure, the bonding layer 115 may be a layer which allows bonding of the microchip 103 to the fluidic substrate 101 at low temperatures and voltages. This is advantageous as these conditions do not damage the CMOS chip, neither do they damage reagents or proteins that may be provided on the fluidic substrate 101 (e.g., microfluidic substrate). According to a specific embodiment, the bonding layer 115 may be a SiO2 or polymer layer.

Figure 19:
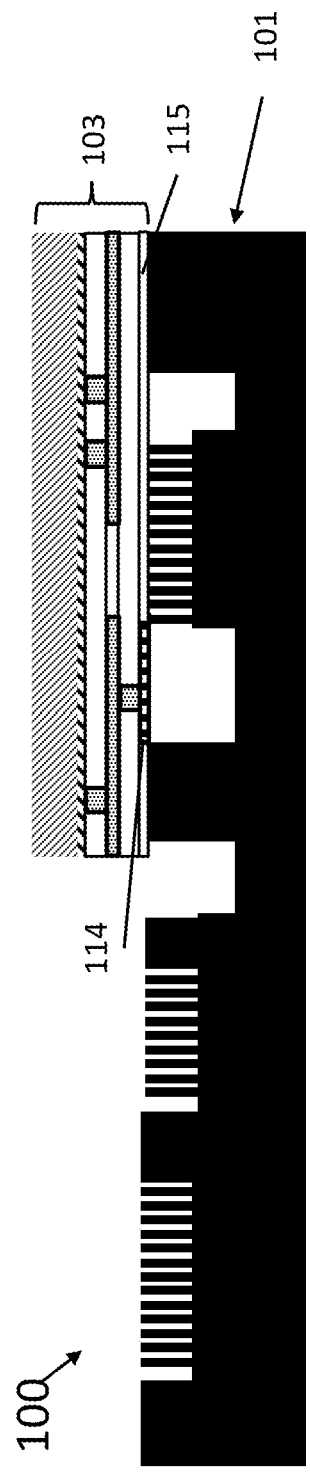
FIG. 19 illustrates the bonding of a CMOS chip with a fluidic substrate, according to an example embodiment.

FIG. 19 illustrates a sensing device 100 according to embodiments of the present disclosure, where a microchip 103, as illustrated in FIG. 18, is bonded to a fluidic substrate 101. The side of the microchip 103 comprising the bonding layer 115 and the electrode 114 is bonded to the side of the fluidic substrate 101 comprising a micro-fluidic component 102. This means that the microchip 103, as illustrated in FIG. 18, is flipped upside down with respect to its position illustrated in FIG. 18. The electrode 114 is thereby in direct contact with a fluid sample present in the micro-fluidic component 102. The bonding layer 115 is used to attach the microchip 103 to the fluidic substrate 101.

Figure 20:
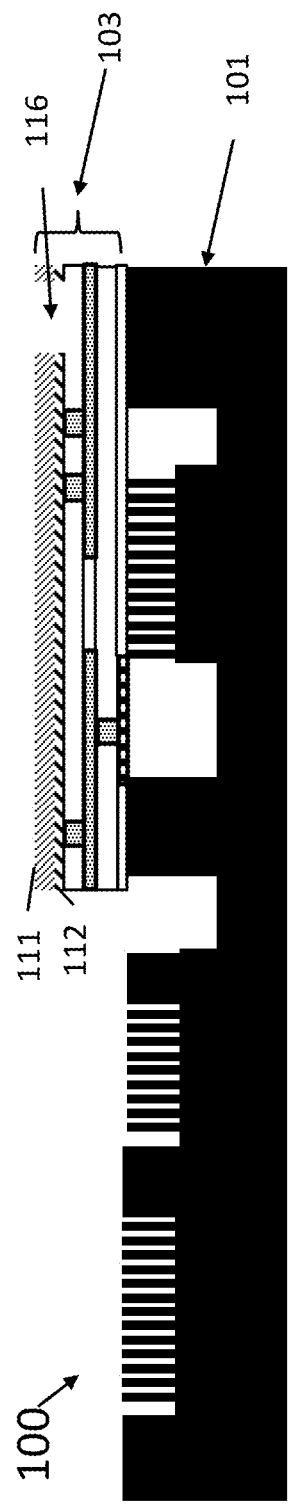
FIG. 20 illustrates the bonding of a CMOS chip with a fluidic substrate, where the CMOS chip comprises a silicon I/O interconnect, according to an example embodiment.

According to embodiments of the present disclosure, the microchip 103 may comprise at least one silicon I/O connection 116, as illustrated in FIG. 20. The silicon I/O connection 116 may be a backside opening through the substrate 111 to access electrical signals of the microchip 103 in the transistor layer 112. Further, in yet alternative embodiments, the silicon I/O connection 116 may be a backside opening through both the substrate 111 and the transistor layer 112 to access electrical signals of the microchip 103 in the interconnection layer 113. FIG. 20 illustrates the sensing device 100 wherein a microchip 103 is bonded to a fluidic substrate 101 and wherein the microchip 103 features a silicon I/O connection 116 through both the substrate 111 and the transistor layer 112.

According to embodiments of the present disclosure, the fluidic substrate may comprise an open micro-fluidic component 102 and the fluidic substrate may be covered partly by the microchip 103. It is advantageous that a part of the micro-fluidic component 102 is not covered as this allows reagents to be applied/spotted on specific open parts of the micro-fluidic component 102. In this case, no extra through-holes are needed to apply reagents after bonding of the fluidic substrate 101 to the microchip 103. It is also advantageous that the chip area is smaller, as the active electronics is the more expensive part of the disposable.

According to embodiments of the present disclosure, the microchip 103 may further comprise at least one I/O pad 117. The at least one I/O pad 117 may be located on the interconnection layer 113.

FIG. 21 illustrates an embodiment of a microchip 103 as a CMOS chip. The microchip 103 comprises a silicon substrate 111. Atop the silicon substrate a transistor layer 112 is present. Atop the transistor layer 112, an interconnection layer 113 is present. The interconnection layer 113 may comprise a plurality of metal layers to interconnect the transistor layer 112 with electrical components. Atop the transistor layer 112, a bonding layer 115, an I/O pad 117 and, in the embodiment illustrated, a plurality of electrodes 114 are present. The electrodes 114 are electrically connected to the transistor layer 112 via the interconnection layer 113. The I/O pad 117 is also electrically connected to the transistor layer 112 via the interconnection layer 113.

According to embodiments of the present disclosure, a first part of a first major surface of the microchip 103 may cover the fluidic substrate 101, a second part of the first major surface of the microchip 103 may not cover the fluidic substrate 101. In these embodiments, the microchip 103 may either be larger than the fluidic substrate 101, or it may be laterally shifted with respect to the fluidic substrate 101 so that a portion of the microchip 103 forms an overhang with respect to the fluidic substrate 101. The second part of the first major surface of the microchip 103 may comprise at least one I/O pad 117 to have access to the I/O pad 117.

FIG. 22 illustrates a microchip 103 (of FIG. 21) bonded to a fluidic substrate 101. A first part of the microchip 103 at least partly, and in the embodiment illustrated fully covers the fluidic substrate 101 wherein electrodes 114 are in direct contact with a fluid sample when present in the micro-fluidic component 102 of the sensing device 100. The bonding layers 115 are used to bond a first part of the microchip 103 to the fluidic substrate 101. A second part of the microchip 103 forms an overhang which does not cover the fluidic substrate 101. The second part comprises the I/O pad 117. As an advantage, this overhang allows easy access to the I/O pad 117. This allows standard I/O pad dimensions and packaging approaches to be used for inserting the substrate in slots typically used for smartcards. It is a further advantage that additional processing steps to fabricate silicon I/O connections (e.g., a hole through the substrate and transistor layer) to access electrical signals in the microchip 103 are not required.

According to embodiments of the present disclosure, the fluidic substrate 101 further comprises at least one optical waveguide to allow optical excitation and sensing of the fluid sample when present in the sensing device 100.

According to embodiments of the present disclosure, the fluidic substrate 101 or the microchip 103 comprises at least one through-hole for application of a biochemical reagent to a region of the micro-fluidic component 102 or to a region of the microchip 103. The through-holes in the fluidic substrate 101 or the microchip 103 allow the application of biochemical reagents to specific regions of the micro-fluidic component 102 or to specific regions of the microchip 103. This is advantageous as it allows reagents to be applied after attachment of the microchip 103 to the fluidic substrate 101.

Figure 23:
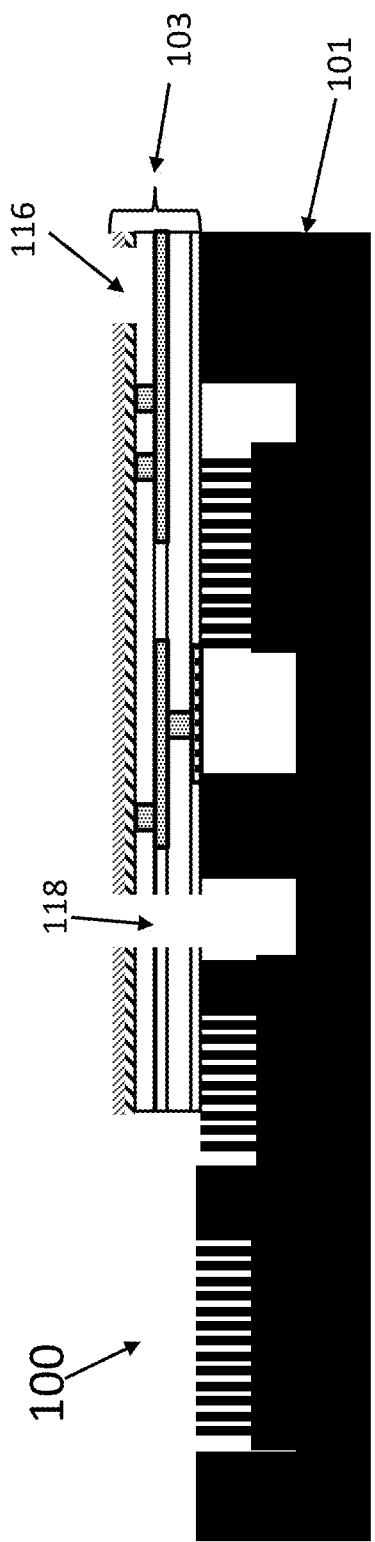
FIG. 23 illustrates the bonding of a CMOS chip with a fluidic substrate, according to an example embodiment.

According to embodiments of the present disclosure, the microchip 103 may comprise at least one through-hole 118. When attached to the fluidic substrate 101, the through hole 118 in the microchip 103 allows reagent spotting on a specific location of the micro-fluidic component 102 in the fluidic substrate 101 or on a specific part of the microchip 103. FIG. 23 illustrates such an embodiment wherein the microchip 103 comprises one through hole 118. In this embodiment, the microchip 103 further comprises a silicon I/O connection 116. As illustrated, the microchip 103 completely covers a part of the fluidic substrate 101.

Figure 24:
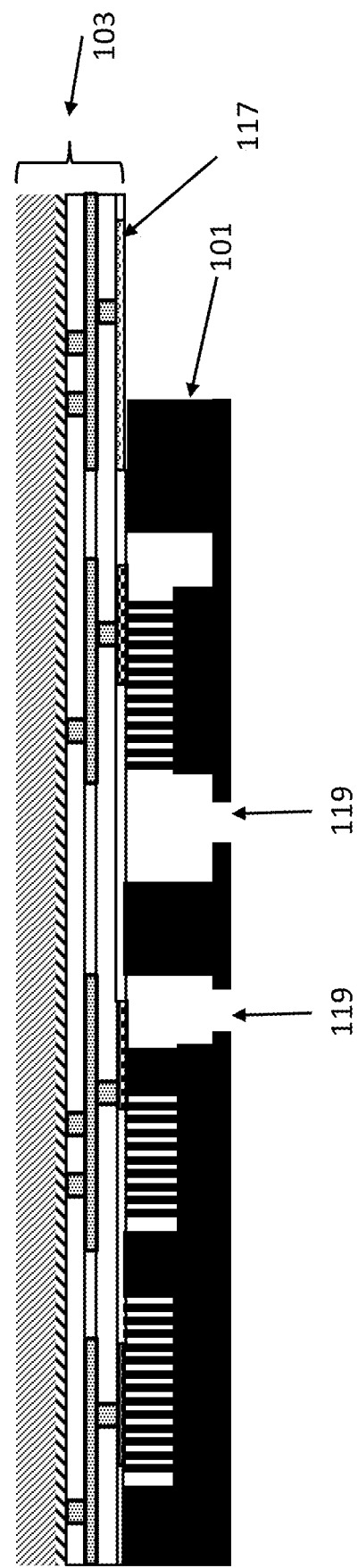
FIG. 24 illustrates the bonding of a CMOS chip with a fluidic substrate, according to an example embodiment.

According to same or alternative embodiments of the present disclosure, a first side of the fluidic substrate 101 comprises the micro-fluidic component 102. The other side, opposite to the side where the micro-fluidic component 102 is provided, may comprise a at least one through hole 119. The through hole 119 allows reagent spotting on a specific location of the micro-fluidic component 102 in the fluidic substrate 101 or on a specific part of the microchip 103. FIG. 24 illustrates such an embodiment wherein the fluidic substrate comprises two through holes 119. A part of the microchip 103 covers the fluidic substrate 101, the part not covering the fluidic substrate 101 but forming an overhang comprises an I/O pad 117.

According to embodiments of the present disclosure, the lid comprising the microchip 103 may be bonded to the fluidic substrate 101 using a polymer, which may preferably be a lithographically patterned polymer. The material for forming the bonding between the microchip 103 and the fluidic substrate 101 should be suitable for perform a Si—Si bonding, preferably at low temperature, such as room temperature. This is compatible with CMOS circuits being present on the lid, which should not be destroyed by the bonding process, and with reagents being present on or in the fluidic substrate 101, which should also not be destroyed by the bonding process. Suitable bonding materials for bonding the microchip 103 to the fluidic substrate 101 are for instance photopatternable PDMS (obtainable from Dow Corning), SU8 (obtainable from Micr Chem), or OSTE (obtainable from Mercene Labs). These bonding materials all have room temperature as bonding temperature.

According to another embodiment of the present disclosure, the lid is bonded to fluidic substrate 101 using a CMOS compatible packaging technique. The use of CMOS packaging techniques may be used when the fluidic substrate 101 is a semiconductor substrate and the lid is a microchip 103, e.g., a CMOS chip.

According to embodiments of the present disclosure, the device 100 may further comprise metal contacts electrically connected to the microchip 103 for reading electrical signals from the microchip 103. The metal contacts may be located on the lid or electrically connected to electronic circuitry in the lid. The position and shape of the metal contacts may be selected according to standards, allowing insertion of the sensing device in standardized slots such as slots for memory cards (e.g., CompactFlash, SmartMedia, MultiMedia Card or Secure Digital (SD) memory cards) commonly used in communication devices such as mobile devices. The insertion of the sensing device 100 in a mobile device allows processing of the electrical signals from the microchip 103 by a processor and/or other electronic components present in the mobile device. For example, a processor of a smartphone may be used to process electrical signals and/or to display data. Further, the sensing device features a data communication interface for sending data, e.g., via custom or standard interfaces like wired interfaces such USB or via wireless communication such NFC or Bluetooth, to a sensing device, personal computer, a computing unit, or smartphone. The sensing device may function as a smartcard for use in communication devices, or as a stand-alone system, or a system where a power interface such as a battery powers electronic circuitry such as a micro-chip in the sensing device. Alternatively, the sensing device may be powered via a communication port of the sensing device.

Figure 33:
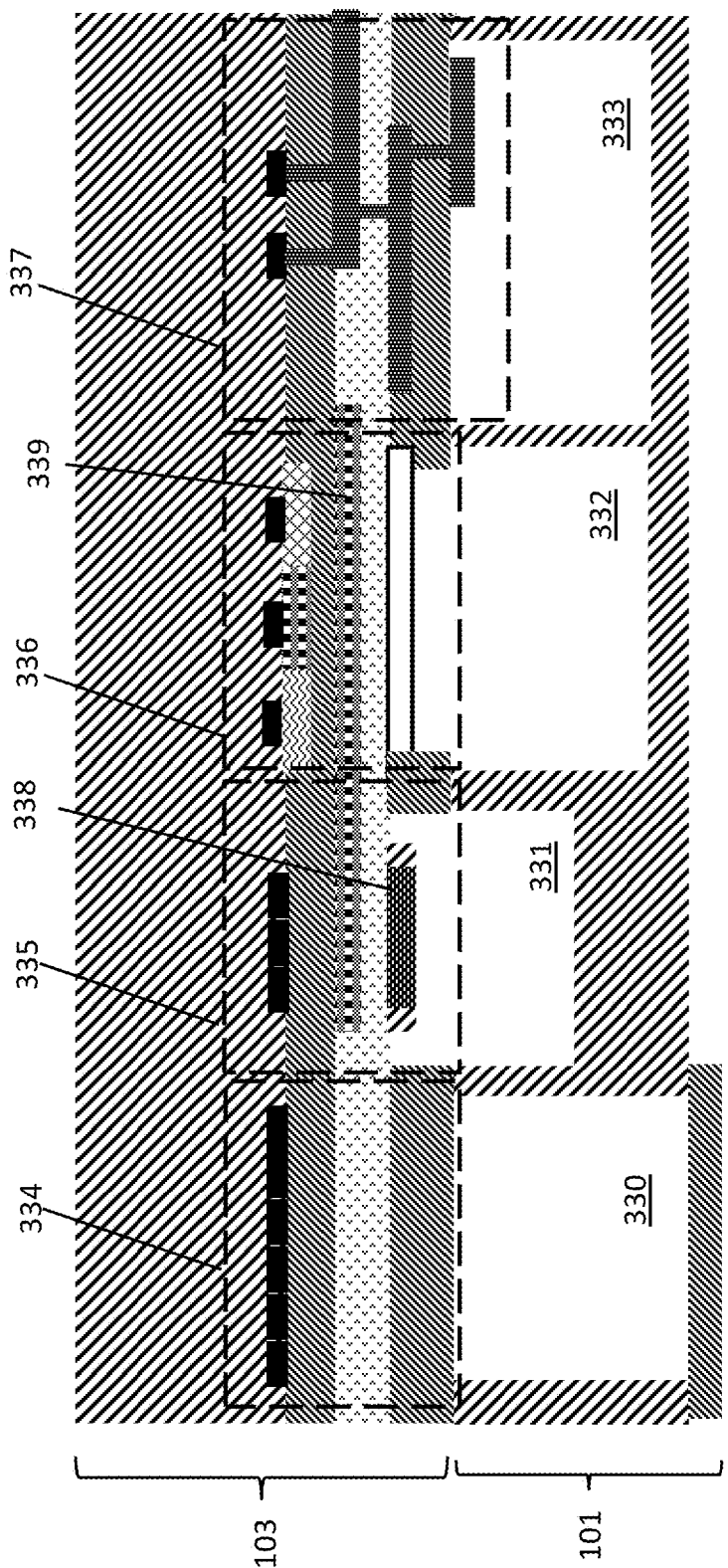
FIG. 33 is a cross-sectional view of a sensing device, according to an example embodiment.

FIG. 33 illustrates a sensing device 100 according to embodiments of the present disclosure, where a fluidic substrate 101 and a microchip 103 are bonded to one another. The fluidic substrate 101 comprises different micro-fluidic components for multi-omic analysis, in the embodiment illustrated comprising a plurality of chambers 330, 331, 332, 333 and microfluidic channels (not illustrated). The chambers may have different depths, depending on their function and the type of measurement being performed. One or more chambers may act as vacuum compartments. The chambers may be separated by valves that may be actuated in any suitable way, for instance by fluidic forces or by electricity. The membrane or valve separating the vacuum compartments from the microfluidic channels may be opened by any suitable way as discussed, such as mechanical action, seal breaking, valve opening, heating, etc. Electrodes for actuation may be provided on the fluidic substrate 101 or on the microchip 103. The CMOS chip forming the lid 3 may thus incorporate different functionalities (e.g., microscopic imager 334 comprising pixels, optical detectors 335, 336 comprising resonators and waveguides 339, and circuitry 337 for heating and/or sensing, filters e.g., for fluorescence, etc). The CMOS microscopic imager 334 may comprise CMOS active pixels for readout of optical signals from the fluid sample in the microfluidic component 102. The CMOS optical detector 335 comprises an optical resonator 338. A waveguide 339 may be present for transporting measurement light from one location of the microchip 103 to another location. The waveguide may for instance be used for irradiating the sample for performing lensfree microscopy. Furthermore, filters may be provided in the fluidic substrate 101 or in the microchip 103 for rejecting optical excitation from emission, so as to enable measurement of a fluorescent signal. Also multispectral filters may be provided in the fluidic substrate 101 or in the lid, for measurement fluorescent signals with multiple colors.

This way, detection of different types of markers can be performed within a single, preferably disposable, sensing device according to embodiments of the present disclosure.

According to embodiments of the present disclosure, the shape of the sensing device 100 allows insertion into a mobile communication device. According to embodiments of the present invention, the sensing device 100 has the shape/dimensions of a memory card. It is an advantage of embodiments of the present invention that the dimensions of the sensing device 100 may be according to standards, e.g., according to standards of memory cards used in mobile devices such as: CompactFlash, SmartMedia, MultiMedia Card, Secure Digital memory cards or any other type. An example of such embodiment can be seen in FIG. 31, in which a needle 104 is present. Metal contacts of the SD card may allow direct readout.

According to embodiments of the present disclosure, at least a part of the fluidic substrate 101 and/or the lid 3 may be fabricated from a transparent material to allow optical inspection of a fluid sample when the fluid sample is present in the micro-fluidic component 102. The part of the fluidic substrate 101 that is fabricated from a transparent material may be part of the micro-fluidic component 102 of the sensing device 100. The transparent part may be a side-wall of the micro-fluidic component 102 of the sensing device 100. The transparent material allows optical inspection of a fluid sample in the sensing device 100.

An optical detector may be used to optically inspect a fluid sample, in order for instance to detect an analyte. The optical detector may be an image sensor which may be part of an external device or may be integrated in the sensing device 100. The transparent material may be a transparent oxide or polymer. For microscopy purposes, a part of the lid or a part of the fluidic substrate 101 may be transparent. For lens-free imaging purposes, a part of the lid and a part of the fluidic substrate 101 may be transparent to enable working in transmission mode wherein a radiation source may be used to radiate an object in a fluid sample in the sensing device 100 through the transparent part of the lid and a detector may be used to detect signals from the radiated object through the transparent part of the fluidic substrate 101. The signals may be diffraction patterns of a radiated object in the fluid sample.

Figure 31:
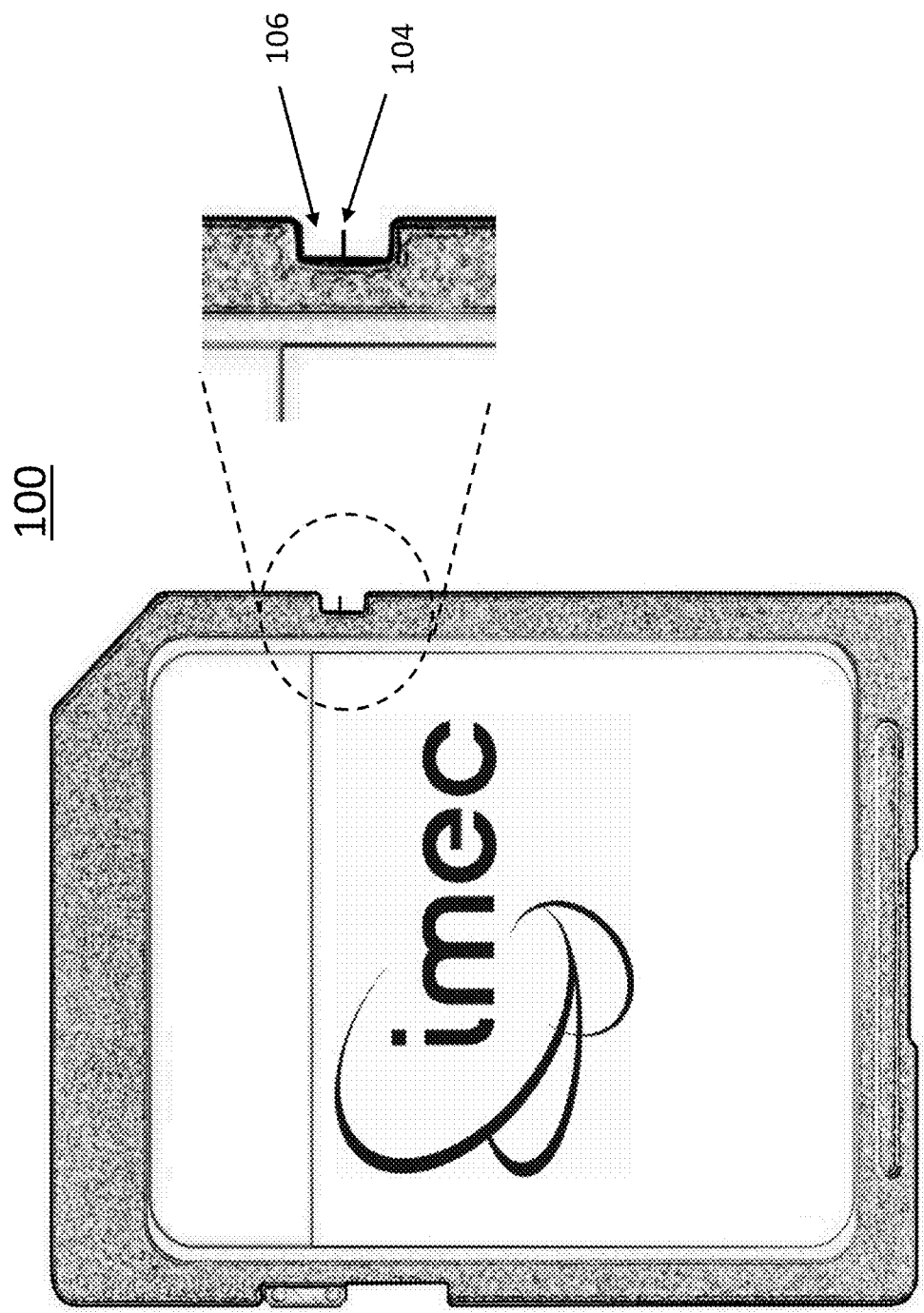
FIG. 31 illustrates a sensing device in the shape of an SD card, according to an example embodiment.
Figure 32:
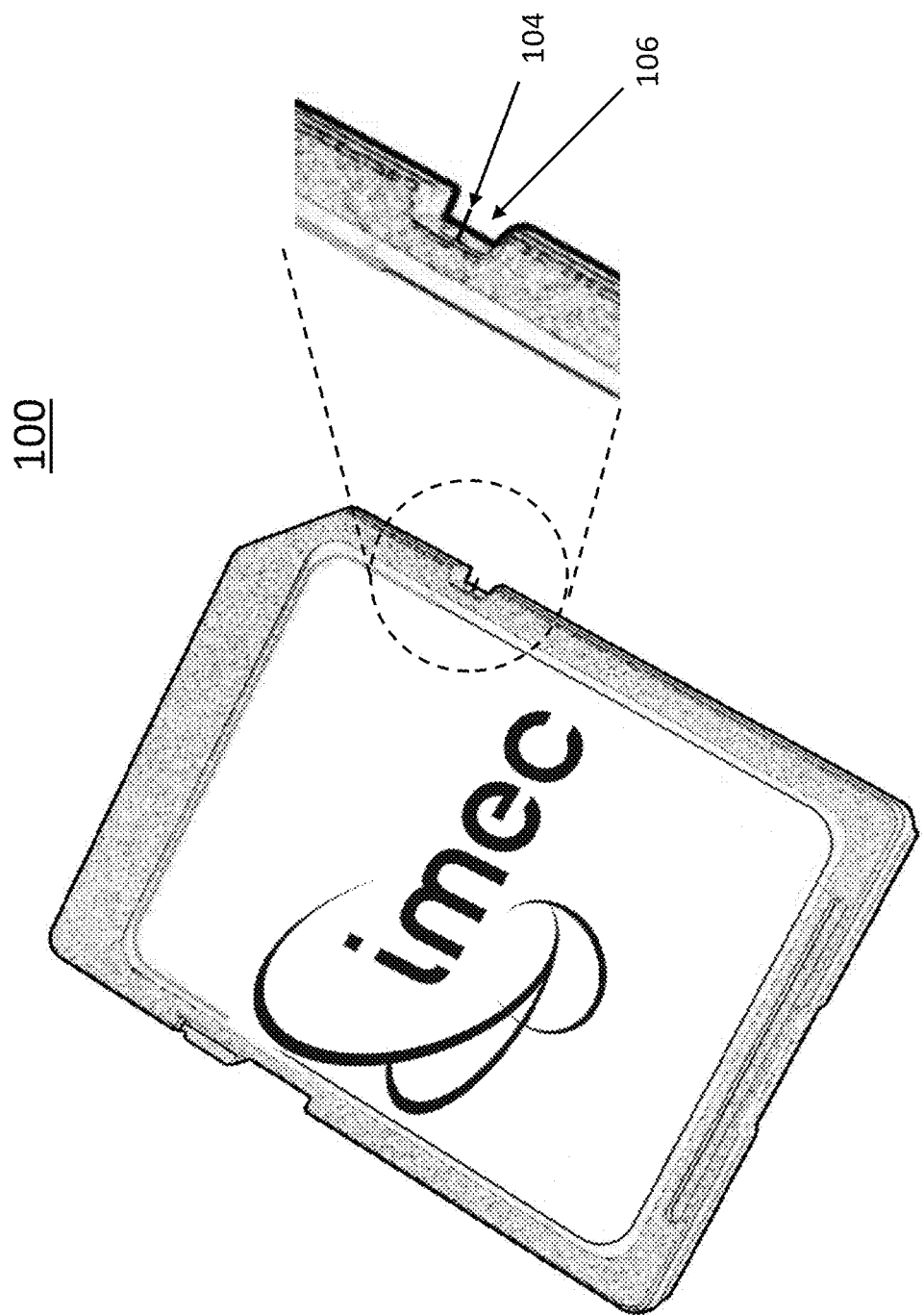
FIG. 32 illustrates another sensing device in the shape of an SD card, according to an example embodiment.

FIG. 31 and FIG. 32 illustrate an embodiment of the present disclosure where the sensing device 100 has the shape of an SD card. Inside the cut-out 106 (which is always present according to SD card standards), a needle 104 is present. At the other side of the SD card, the metal contacts are present and electrically connected to the microchip 103 to allow read-out of electrical signals from the microchip 103 which may be further processed by the device in which the SD card is inserted.

According to embodiments of the present disclosure, the lid 3 or the fluidic substrate 101 may further comprise a compartment for powering the sensing device 100, such as a battery compartment (not illustrated) which is electrically connected to the lid 3.

According to another aspect, the disclosure relates to a method to fabricate a sensing device 100 as disclosed in other aspects of the present disclosure. The method comprises: providing a fluidic substrate 101; providing a lid 3; attaching the fluidic substrate 101 to the lid 3 to close the fluidic substrate 101 at least partly. And the fluidic substrate 101 is a silicon fluidic substrate and the lid 3 comprises a CMOS chip, and the fluidic substrate 101 is attached to the lid 3 using a CMOS compatible bonding process.

It is advantageous that the fluidic substrate 101 is bonded to the lid 3 using a CMOS compatible bonding process. In state of the art devices, bonding is performed using high temperature/voltage bonding techniques. These bonding techniques may damage electronic circuitry present in the CMOS chip and/or reagents present in the fluidic substrate 101 (e.g., microfluidic substrate). The use of a CMOS compatible bonding enables bonding at lower temperatures/voltages and therefore preserves the electronic circuitry of the microchip 103 and the reagents present in the fluidic substrate 101 (e.g., microfluidic substrate). According to embodiments of the present disclosure, the bonding may be performed via a wafer to wafer or die to wafer bonding process such as direct oxide to oxide bonding or bonding via a pattern-able polymer. Additionally, it can also be advantageous to be able to perform the bonding at a low temperature in case some reagents are already spotted on one of the substrates during the fabrication flow.

The fluidic substrate 101 may be fabricated using a combination of coarse and fine structures in a single piece of silicon substrate by a combination of two hard masks, protection and de-protection of layers, and etching of coarse and etching of fine structures. The fine structures may be structures configured to enable a controlled capillary suction in the micro-fluidic component 102 of the sensing device 100. The fine structures may comprise micro-pillars 270 and/or other microstructures. The coarse structures may be structures for storing larger volumes of fluids e.g., reagent storage 102b for storing reagents, or a wick 102i. It is an advantage to use silicon since the very high anisotropic etching of silicon results in fine structures with extremely high aspect ratios. The silicon micro-pillars 270 typically have lateral dimensions from 1 um to 20 um with aspect ratios of 20-50. High aspect ratios are advantageous in having a high surface to volume ratio, essential for capillary flow. The high aspect ratio fine structures, combined with the coarse structures allow implementation of more complex capillary fluidic functions in a more compact footprint than is achievable with any other material. More complex functions include separation (e.g., cells from molecules), mixing, valving, and thermally controlled reactions. Moreover, silicon is an inert material with clear advantages towards implementation of biochemical reactions. The advantage of the extremely compact fully integrated disposable device results from the advanced use of silicon for both the fluidic substrate and the CMOS lid. The reduced footprint also results in reduced cost of the entire sensing device.

According to embodiments of the present disclosure, providing a fluidic substrate 101 comprises providing a silicon substrate 201, illustrated in FIG. 11, and patterning the silicon substrate to form a micro-fluidic component 102 and a means for providing a fluid sample in the sensing device 100, the micro-fluidic component 102 being configured to propagate a fluid sample via capillary force through the sensing device 100.

According to embodiments of the present disclosure, providing a fluidic substrate 101 comprises: providing a silicon substrate 201, providing an oxide mask 202, and patterning the oxide mask 202 by using a first patternable mask layer 210, so as to create fine structures 203 in the oxide mask 202 (shown in FIG. 12). Providing a fluidic substrate 101 further comprises providing a protection layer 204 to protect the patterned oxide mask, patterning coarse structures in a second patternable mask layer 211 (shown in FIG. 13), etching of the coarse structures 205 in the silicon substrate 201 through the second mask layer 211 (shown in FIG. 14), removing the second mask layer 211 and growing oxide 206 (shown in FIG. 15) for protecting the coarse structures 205, removing the protection layer 204 (shown in FIG. 16) and etching the fine structures 203 using the oxide layer 206 as an etch mask (shown in FIG. 16), and removing the oxide 206 (shown in FIG. 17). The resulting structure is a fluidic substrate 101 (e.g., microfluidic substrate), which may be used in a sensing device according to embodiments of an aspect of the present disclosure.

FIGS. 11-17 illustrate how the fluidic substrate 101 may be fabricated. According to embodiments of the present disclosure, the fluidic substrate 101 may be fabricated by performing:

Patterning fine structures 203 comprising: providing a silicon substrate 201, providing an oxide mask 202, patterning the oxide mask 202 to create fine structures 203 in the oxide mask 202; providing a protection layer 204 to protect the oxide 202; performing lithography of coarse structures 205; performing etching of the coarse structures 205; growing oxide 206 for protecting the coarse structures 205 wherein the protection layer 204 on the fine structures 203 prevents oxide growth; removing the protection layer 204 and etch the fine structures 203; removing the oxide 206.

According to embodiments of the present disclosure, the protection layer 204 may be a nitride layer.

One or more of the coarse structures may be hermetically closed with a sacrificial element (such as a membrane) under pressure, thereby providing a vacuum chamber. A mechanism for opening the chamber may optionally be provided in the manufacture process of a device according to the present disclosure.

According to embodiments of the present disclosure, providing the microchip 103 comprises: providing a silicon substrate 111, fabricating a transistor layer 112 atop the silicon substrate and providing an interconnection layer 113 atop the transistor layer. The interconnection layer may comprise at least one metal layer. The microchip 103 is fabricated using standard CMOS process techniques.

Further, on top of standard CMOS process flows, additional components may be deposited or patterned on the interconnection layer 113 such as biocompatible electrodes, a bonding layer, I/O pads or other components.

According to embodiments of the present disclosure, through holes 119, 118 may be etched through the fluidic substrate 101 or the microchip 103 to enable fluidic access for applying of reagents to the fluidic substrate 101 or microchip 103. The through-holes in the microchip 103 may be fabricated whilst fabricating silicon I/O interconnections 116 in the microchip 103. The through-holes in the fluidic substrate 101 may be fabricated by first thinning the fluidic substrate 101 and then etching the through-holes.

According to embodiments of the present disclosure, the microchip 103 may be bonded to the fluidic substrate 101 using a die to wafer or wafer to wafer bonding process.

To access electrical signals of the microchip 103, silicon I/O contacts 116 may be provided. According to embodiments of the present disclosure, the contacts may be fabricated by thinning the silicon substrate 111 of the microchip 103 and performing a back side etching on the silicon substrate 111 to gain access to a metal layer of the interconnection layer 113.

Alternatively, a microchip 103 comprising an I/O pad 117 at a first side of the microchip 103 may be provided, wherein the first side of the microchip 103 is bonded to the fluidic substrate 101 and wherein the first side of the microchip 103 comprising the I/O pad 117 does not cover the fluidic substrate 101. This is for example illustrated in FIG. 22. The I/O pad 117 is accessible when the microchip 103 is bonded to the fluidic substrate 101. The I/O pad 117 may be used as a metal contact on a memory card.

According to embodiments of the present disclosure, the microchip 103 is bonded to the fluidic substrate 101 while aligning at least one electrical component on a first side of a microchip 103 with the micro-fluidic component 102. For example, sensing and actuating electrodes on the first side of the microchip 103 are aligned with a sensing or actuation side in the fluidic substrate 101. This allows direct contact of a fluid sample with electrical components present on the microchip 103 when a fluid sample is present in the sensing device 100.

According to embodiments of the present disclosure, surfaces of the fluidic substrate 101 and the lid are partially or fully coated to modify surface interactions with the fluid sample. The surfaces may be inner surfaces of the micro-fluidic component 102 or a surface of the microchip 103 that is bonded to the fluidic substrate 101. In particular those parts of the surface of the microchip 103 that are in contact with a fluid sample present in the micro-fluidic component 102. The coating may be a hydrophilic coating.

The surfaces of the micro-fluidic component 102 and/or the side of the microchip 103 bonded to the fluidic substrate 101 can be made hydrophilic in order to improve the wetting behavior of the surfaces, thereby promoting capillary flow. The surfaces can also be treated in order to avoid absorption or adhesion of biomolecules on the walls. The coating can be done for example by vapor coating with silanes. According to embodiments of the present disclosure, the coating may be performed locally on certain parts of the fluidic substrate 101 (e.g., in some micro-fluidic channels) or on certain parts of the microchip 103.

According to embodiments of the present disclosure, at least one through-hole is fabricated in the fluidic substrate 101 by first etching the through-hole and then filling the through-holes with a transparent oxide of polymer.

Embodiments of the present disclosure improve the functionality, portability and manufacturability of compact disposable point of care devices. A particular embodiment of the present disclosure is a fully integrated silicon device with a needle or an inlet for the intake of blood or any other body fluid. The sensing device features a capillary fluidic system for the propagation of a fluid sample through the sensing device via capillary action. A capillary pump functioning as the wicking zone of the capillary fluidic system may be used to propagate the fluid sample in the sensing device. A sensor chip reading signals produced by biochemical sensing reactions inside the capillary system may be used to add biosensing functionality to the sensing device. Further, the sensing device features a data communication interface for sending data to a personal computer, a computing unit, smartphone or any other wireless communication sensing device. The sensing device may function as a stand-alone system wherein a power interface such as a battery powers electronic circuitry such as a micro-chip in the sensing device. Alternatively, the sensing device may be powered via a communication port of the sensing device.

The sensing device may further comprise fluidic manipulation structures including filtering, mixing, valves structures. A protection structure with a cut off zone to protect and prevent breaking the needle before usage may be present to avoiding contamination before usage. Structures such as electrically controllable fluidic manipulation structures including electrowetting, electro and dielectrophoretic manipulation may be present to interact with a fluid sample in the sensing device. Electronic controllable heaters may be present for accurately controlling the temperature of the chip or for thermal cycling purposes.

Another exemplary embodiment of the present disclosure includes a low cost and compact manner to fabricate all of the above functions by providing a semiconductor substrate (e.g., silicon substrate) which may comprise lithographically defined channels, micro-pillars and microstructures of various shapes fabricated by deep Reactive Ion Etching and designed to function as a capillary fluidic platform. The silicon substrate may have a provision for making a needle and a cut off zone for protecting the needle. The silicon substrate can have different etch depths allowing for precise control over the volume and capillary flow of a fluid sample in the sensing device. The silicon substrate may be closed by a CMOS substrate (e.g., microchip 103) comprising CMOS electronics containing a transistor layer. The electronics may be designed to provide functionality including sensing, actuating, signaling, data processing and data communication and therefore replaces the point of care instrument. Some of the electrodes may be in direct contact with the fluid, these electrodes may be protected in a fluid compatible manner. The silicon substrate may be closed by the CMOS substrate by bonding both substrates in a leakage free and biocompatible manner. This can be done via a wafer to wafer or die to wafer bonding process such as bonding via a patternable polymer. The inner silicon substrate surfaces which may be in contact with the body fluids may feature a hydrophilic layer via coating of the inner channels. Additionally, through wafer holes may be fabricated in the silicon substrate for supplying reagents after the sensing device has been bonded. For each analysis, different reagents can be supplied. As an advantage, the same device becomes configurable for different diseases by simply adding reagents through the through-holes in the last production step. The through holes may be sealed when obtaining the sample via the inlet and propagating it through the microfluidic component. The sensing device may be manufactured using CMOS compatible processing steps which lower production cost and enable the sensing device to be used as disposable device.

Further, the sensing device may comprise components to enable interfacing with standard user interfaces. For example, the use of such a sensing device as a smartcard in wireless communication devices inserted in slots typically foreseen for smartcards. For example, the use of such a sensing device together with a compact and cheap battery and low cost communication device (e.g., Bluetooth, NFC). For example, the use of such a sensing device together with a wired communication interface (e.g., USB).

Embodiments of the present invention may be used to detect DNA/RNA from body fluids and perform an analysis to detect: mutations (ancestry, drug dosing, disease predisposition), miRNA (marker for cancer and other diseases), pathogen DNA/RNA (infectious diseases such as HepC, HIV, etc.), microbiome DNA. Further, the sensing device may be used to detect proteins such as biomarkers for a specific disease (cancer, Alzheimer's, infectious diseases, heart disease, cancer etc.). Further, the sensing device may be used to detect small molecules and metabolites to reveal metabolic information (cholesterol). Further, the sensing device may be used to detect biomarkers from exosomes. Further the sensing device may be used to perform microscopy to perform a blood count, analyze cells present in the blood (e.g., circulating tumour cells), identify infectious agents (e.g., malaria), and to detect blood disorders (e.g., sickle cell anemia).

What is claimed is:

1. A fluid analyzing device comprising:
   a sensing device for analyzing a fluid sample, the sensing device comprising:
   a microchip configured for sensing the fluid sample; and
   a micro-fluidic component for propagating the fluid sample to the microchip;
   an inlet coupled to the micro-fluidic component, wherein the inlet is configured for providing the fluid sample to the micro-fluidic component;
   a switch electrically coupled to an on-board energy source; and
   a vacuum compartment air-tight connected to the sensing device, wherein the vacuum compartment comprises a sacrificial element separating the vacuum compartment from the sensing device, wherein the on-board energy source electrically drives the sacrificial element to cause the vacuum compartment to open when the switch is actuated, and wherein opening the vacuum compartment creates a suction force in the micro-fluidic component suitable for propagating the fluid sample through the micro-fluidic component when the sacrificial element is broken.

2. The fluid analyzing device of claim 1, further comprising:
   a package comprising the sensing device, the inlet, and the vacuum compartment.

3. The fluid analyzing device of claim 1, further comprising a movable structure for breaking the sacrificial element.

4. The fluid analyzing device of claim 3, wherein the movable structure comprises a mechanical structure coupled to a needle inside the vacuum compartment, wherein the mechanical structure comprises a spring configured to actuate the needle, and wherein the needle is configured to break the sacrificial element when actuated.

5. The fluid analyzing device of claim 1, further comprising a heating element positioned such that the sacrificial element is broken by way of heat from the heating element.

6. The fluid analyzing device of claim 5, wherein the heating element is positioned in or on the sacrificial element.

7. The fluid analyzing device of claim 5, wherein the heating element is positioned on a substrate comprising the micro-fluidic component.

8. The fluid analyzing device of claim 1, wherein the microchip is a CMOS chip, and wherein the sensing device further comprises:
   a silicon fluidic substrate comprising the micro-fluidic component embedded in the silicon fluidic substrate, wherein the silicon fluidic substrate is fluidically connected to the inlet.

9. The fluid analyzing device of claim 8, wherein the CMOS chip comprises a transistor layer, the transistor layer being electrically connected to at least one electrical component, the electrical component being at least one of: biosensing circuitry, electrodes for sensing purposes, electrodes for fluid manipulation purposes, circuitry for data communication purposes, circuitry for wireless data communication purposes, temperature sensors, heater electrodes for temperature control, and fluid sensors and electrodes for fluidic viscosity control.

10. The fluid analyzing device of claim 8, wherein the CMOS chip is a lid attached to the silicon fluidic substrate, and wherein the CMOS chip at least partly covers the silicon fluidic substrate and at least partly closes the micro-fluidic component.

11. The fluid analyzing device of claim 1, further comprising:
    a sealing layer disposed between the sensing device and the vacuum compartment, wherein the sealing layer bonds the vacuum compartment to the sensing device.

12. A method for sensing a fluid sample, comprising:
    providing a fluid analyzing device comprising:
    a sensing device comprising:
    a microchip configured for sensing the fluid sample; and
    a micro-fluidic component for propagating the fluid sample to the microchip;
    an inlet coupled to the micro-fluidic component, wherein the inlet is configured for providing the fluid sample to the micro-fluidic component;
    a switch electrically coupled to an on-board energy source; and
    a vacuum compartment air-tight connected to the sensing device, wherein the vacuum compartment comprises a sacrificial element, separating the vacuum compartment from the sensing device, wherein the on-board energy source electrically drives the sacrificial element to cause the vacuum compartment to open when the switch is activated, and wherein opening the vacuum compartment creates a suction force in the micro-fluidic component suitable for propagating a fluid sample through the micro-fluidic component when the sacrificial element is broken; and
    providing a fluid sample to the micro-fluidic component;
    detecting the fluid sample being provided to the micro-fluidic component;
    opening the vacuum compartment when the fluid sample is detected;
    propagating the fluid sample through the micro-fluidic component by opening the vacuum compartment thereby creating a pressure difference between the vacuum compartment and the micro-fluidic component; and
    sensing the fluid sample using the sensing device.

* * * * *